United States Patent
Bogyo et al.

(10) Patent No.: US 10,100,037 B2
(45) Date of Patent: Oct. 16, 2018

(54) ACTIVITY-BASED PROBE COMPOUNDS, COMPOSITIONS, AND METHODS OF USE

(71) Applicant: THE BOARD OF TRUSTEES OF THE LELAND STANFORD JUNIOR UNIVERSITY, Palo Alto, CA (US)

(72) Inventors: Matthew S. Bogyo, Redwood City, CA (US); Martijn Verdoes, Nijmegen (NL)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 211 days.

(21) Appl. No.: 14/777,024

(22) PCT Filed: Mar. 15, 2014

(86) PCT No.: PCT/US2014/029990
§ 371 (c)(1),
(2) Date: Sep. 15, 2015

(87) PCT Pub. No.: WO2014/145257
PCT Pub. Date: Sep. 18, 2014

(65) Prior Publication Data
US 2016/0039792 A1    Feb. 11, 2016

Related U.S. Application Data

(60) Provisional application No. 61/794,296, filed on Mar. 15, 2013.

(51) Int. Cl.
| | |
|---|---|
| *A61B 5/00* | (2006.01) |
| *A61B 8/00* | (2006.01) |
| *A61B 10/00* | (2006.01) |
| *C07D 401/14* | (2006.01) |
| *A61K 49/00* | (2006.01) |

(52) U.S. Cl.
CPC ........ *C07D 401/14* (2013.01); *A61K 49/0034* (2013.01); *A61K 49/0041* (2013.01); *A61K 49/0032* (2013.01)

(58) Field of Classification Search
None
See application file for complete search history.

(56) References Cited

U.S. PATENT DOCUMENTS

| | | |
|---|---|---|
| 5,055,451 A | 10/1991 | Krantz et al. |
| 9,763,577 B2 | 9/2017 | Lee et al. |
| 2002/0028774 A1 | 3/2002 | Karanewsky et al. |
| 2002/0052323 A1 | 5/2002 | Wang |
| 2007/0036725 A1 | 2/2007 | Bogyo et al. |
| 2014/0276103 A1 | 9/2014 | Lee et al. |
| 2014/0301950 A1 | 10/2014 | Lee et al. |

FOREIGN PATENT DOCUMENTS

| | | |
|---|---|---|
| EP | 272671 A2 | 6/1988 |
| JP | 63-253061 A | 10/1988 |
| JP | 2002519406 A | 7/2002 |
| WO | 9641638 | 12/1996 |
| WO | 0001666 A1 | 1/2000 |
| WO | 2009124265 A1 | 10/2009 |
| WO | 2012021800 A2 | 2/2012 |
| WO | 2012118715 A2 | 9/2012 |

OTHER PUBLICATIONS

Verdoes et al. (Chem. Biol. 2012, 19, 619-628).*
Shao, Q.; Yang, Y.M.; Xing, B.G. Chemistry of Optical Imaging Probes. In Molecular Imaging Probes for Cancer Research; World Science: British Columbia, Canada, 2010. Chapter 14.*
Blum et al. (2009) PLoS One 4:e6374.
Blum et al. (2007) Nat. Chem. Biol. 3:668-77.
Verdoes et al. (2012) Chem. Biol. 19:619-28.
Deu et al. (2010) Chem Biol. 17:808-819.
McGrath et al. (1998) Protein Science 7:1294-1302.
Pinitglang et al. (2012) Procedia Computer Science 11:63-74.
Verdoes et al. (2013) J. Am. Chem. Soc. 135:14726-14730.
Xing et al. (2005) J. Am. Chem. Soc. 127:4158-4159.
Brak et al. (2010) J. Med. Chem. 53:1763-73.

* cited by examiner

*Primary Examiner* — Michael G Hartley
*Assistant Examiner* — Melissa J Perreira
(74) *Attorney, Agent, or Firm* — David A. Roise; VLP Law Group LLP

(57) ABSTRACT

Activity-based probe compounds for use in labeling a cysteine protease are provided. The compounds are targeted to the protease through a specific targeting element. The compounds additionally include a detectable element, such as a fluorescent label, a radiolabel, or a chelator. In some cases, the compounds additionally include a quenching element that is released upon reaction with the protease. Also provided are compositions comprising the compounds and methods for using the compounds, for example in labeling a protease in an animal and in visualizing a tumor in an animal.

22 Claims, 8 Drawing Sheets

ACTIVITY-BASED PROBE COMPOUNDS, COMPOSITIONS, AND METHODS OF USE

CROSS-REFERENCE TO RELATED APPLICATION

This application is a national stage application of PCT International Application No. PCT/US2014/029990, filed Mar. 15, 2014, which claims the benefit of U.S. Provisional Application No. 61/794,296, filed on Mar. 15, 2013, the disclosures of which are incorporated herein by reference in their entireties.

STATEMENT OF GOVERNMENTAL SUPPORT

This invention was made with government support under contract EB005011 awarded by the National Institutes of Health. The government has certain rights in the invention.

BACKGROUND OF THE INVENTION

A variety of techniques are currently being developed for use in the areas of molecular imaging and disease monitoring. In particular, optical fluorescence imaging is an approach that is beginning to show promise as a clinical tool, given its sensitivity, specificity, and non-invasiveness. The specificity of fluorescent optical probes may in some cases be provided by their biological targets. For example, optical probes that are recognized by enzyme targets in a biological sample often generate extremely specific signals if the fluorescence of the probe is only unleashed upon enzymatic reaction. Ideally, the fluorescent portion of the probe remains associated with its enzymatic target, even after the fluorescent signal has been activated by the enzymatic reaction. Such fluorescent activity based probes (ABPs) have been described for protease targets. Blum et al. (2009) PLoS One 4:e6374; doi:10.1371/journal.pone.0006374. The ABPs can be distinguished from simple fluorogenic substrates by the permanent covalent bond that results from reaction of the ABP with the enzyme's active site catalytic residue. Although fluorescent substrates may appear to be advantageous due to the signal amplification resulting from the catalytic turnover by their target enzyme, APBs have been found to display increased kinetics of tissue uptake and prolonged retention of probe in the target tissue due to their covalent modification of the target enzyme.

Among the target enzymes of interest for use with fluorescence-based optical probes are proteases, and in particular cysteine proteases. The cysteine cathepsins are a family of proteases that play important roles in health and disease. Reiser et al. (2010) *J. Clin. Invest.* 120:3421-31 Although their function has mainly been described as being confined to the endosomal pathway, evidence is accumulating they are a major regulators of matrix degradation, suggesting that they also function in an extracellular context. Bromme & Wilson (2011) *Role of Cysteine Cathepsins in Extracellular Proteolysis. Biology of Extracellular Matrix Volume 2* 23-51. In addition, members of the cysteine cathepsin family have been shown to be major players in the development and progression of several types of cancer. Mohamed & Sloane (2006) *Nat. Rev. Cancer* (2006) 6:764-75; Palermo & Joyce (2008) *Trends Pharmacol. Sci.* 29:22-8. Furthermore, changes in the expression of the endogenous inhibitors of the cathepsins, the cystatins, have been observed in cancer. Cox (2009) *Cystatins and cancer. Front. Biosci.* 14:463-74. These observations, in combination with potential changes in the intra- and extracellular milieu, stress the importance of tools that allow the direct assessment of the activity of these proteases in the context of a native tumor microenvironment. Several ABPs targeting the cysteine cathepsin family have been synthesized. Edgington et al. (2011) *Curr. Opin. Chem. Biol.* 15:798-805. In particular, the fluorescently quenched ABPs (qABPs) have proven to be powerful tools for non-invasive optical imaging of cancer and subsequent characterization of the target cathepsins on a histological, cellular and protein level. Blum et al. (2007) *Nat. Chem. Biol.* 3:668-77; Verdoes et al. (2012) *Chem. Biol.* 19:619-28.

Activity-based inhibitors of dipeptidyl peptidase I based on a 2,3,5,6-tetrafluorophenoxyarylmethyl ketone reactive group have been reported (Deu et al. (2010) Chem Biol. 17:808-819), but these inhibitors were non-peptidic and did not include a detectable group.

Quenched activity-based peptidic inhibitors for use in the fluorescent imaging of cells containing active proteases such as cathepsin have also been reported. See, e.g., U.S. Patent Application Publication No. 2007/0036725. These probes employ an ester-linked acyloxymethyl ketone reactive group to bind to the protease active site. In some cases, the activity-based fluorescent probes are non-peptidic. See, e.g., PCT International Publication No. WO 2012/118715. In some cases, the activity-based probes are used to radiolabel their target enzymes. See, e.g., PCT International Publication No. WO 2009/124265.

There remains a need in the field, however, for novel activity-based fluorescent probes of cysteine proteases that have higher cellular uptake, that target a broader spectrum of cysteine protease activities, and that offer increased sensitivity of detection.

SUMMARY OF THE INVENTION

The present invention addresses these and other problems by providing compounds, compositions, and methods of use of the compounds and compositions for labeling a cysteine protease.

In particular, according to one aspect of the invention, compounds are provided as represented by structural formula (I):

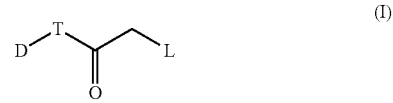

wherein
L is an ether-linked leaving element;
T is a targeting element; and
D is a detectable element.

In some embodiments of the invention, the D group is a fluorescent label, a radiolabel, or a chelator.

In specific embodiments, the D group is a fluorescent label, and even more specifically is a fluorescein, an Oregon green, a bora-diaza-indecene, a rhodamine, or a cyanine label. In even more specific embodiments, the fluorescent label is a cyanine label, such as Cy5.

In some embodiments of the invention, the T group targets the compound to a cysteine protease. In certain embodiments the T group is a non-peptidic targeting element, such as an element comprising a triazole structure, including, for example, various specific compounds comprising a triazole structure. In certain other embodiments, the T group is a peptidic targeting element.

In some compound embodiments, the D-T- group is

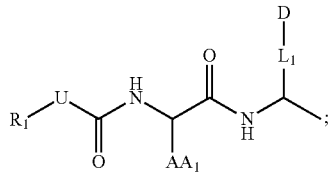

wherein $L_1$ is a linker;
$AA_1$ is an amino acid side chain;
U is O, N, or S;
$R_1$ is alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, or a protecting group, and is optionally substituted with 1 to 3 A groups; and
each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamido, or azido.

In specific compound embodiments, $L_1$ is an optionally substituted alkyl linker, wherein each carbon atom is optionally replaced with a heteroatom.

In other specific compound embodiments, $AA_1$ is an aralkyl amino acid side chain, optionally substituted with 1 to 3 A groups.

In still other specific compound embodiments, U is O.

In certain embodiments, the D group is a fluorescent label, a radiolabel, or a chelator.

In specific embodiments, the D group is a fluorescent label, and even more specifically is a fluorescein, an Oregon green, a bora-diaza-indecene, a rhodamine, or a cyanine label. In even more specific embodiments, the fluorescent label is a cyanine label, such as Cy5.

In some compound embodiments, the L group comprises a quencher, and in more specific embodiments, L is $L_2$-$L_3$-Q, wherein $L_2$ is a phenoxy group, $L_3$ is a linker, and Q is a quencher.

In specific embodiments, L is

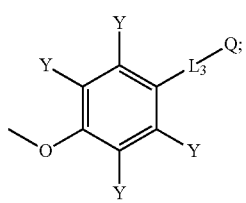

wherein each Y is independently an electron-withdrawing group or hydrogen.

In more specific embodiments, each Y is independently a halogen or hydrogen, and in even more specific embodiments, L is

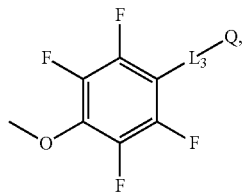

and
$L_3$ is an optionally substituted alkyl linker, wherein each carbon atom is optionally replaced with a heteroatom.

In even more specific embodiments, L is

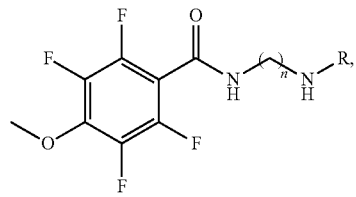

wherein
R is a QSY quencher, and n is an integer from 1 to 16.

In preferred embodiments, the QSY quencher is a hydrophilic QSY quencher, and more specifically, the hydrophilic QSY quencher is a sulfo-QSY quencher.

In some embodiments of the invention, compounds are provided as represented by structural formula (II):

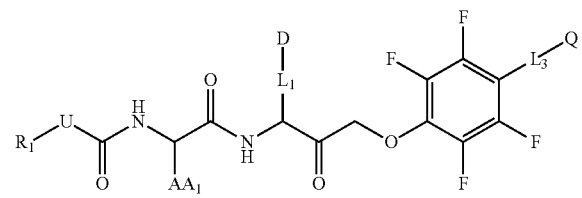

(II)

wherein D is a fluorescent label, $L_3$ is a linker, and Q is a quencher.

In more particular embodiments, compounds are provided as represented by structural formula (III):

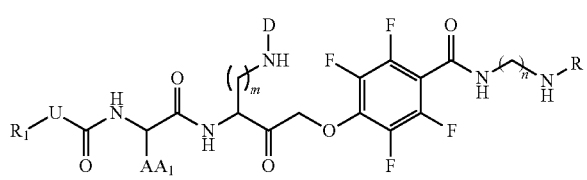

(III)

wherein R is a QSY quencher, D is a cyanine dye, and m and n are independently integers from 1 to 16. The R group may, in some of these embodiments, be QSY21 or sulfo-QSY21, and the D group may be Cy5.

Specific compound embodiments of the invention include the following:

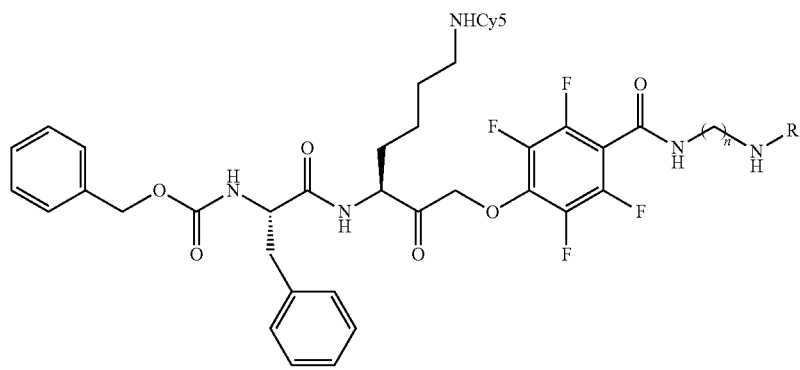

wherein
R=QSY21 and n=6;
R=Sulfo-QSY21 and n=6;
R=QSY21 and n=2; and
R=Sulfo-QSY21 and n=2.

According to another aspect, the invention provides compositions for use in labeling a protease in an animal comprising a compound of the instant disclosure and a pharmaceutically acceptable carrier.

According to yet another aspect, the invention provides methods of labeling a protease in an animal comprising the step of:
administering a composition of the instant disclosure to the animal.

The invention still further provides methods of visualizing a tumor in an animal comprising the steps of:
administering a composition of the instant disclosure to the animal, and measuring a detectable signal generated in the animal from a reaction of the composition with a cathepsin cysteine protease, wherein the detectable signal is associated with a tumor in the animal.

In specific method embodiments, the detectable signal is a fluorescent signal. In other specific method embodiments, the fluorescent signal is generated at a tumor margin.

DETAILED DESCRIPTION OF THE INVENTION

Figure 1:
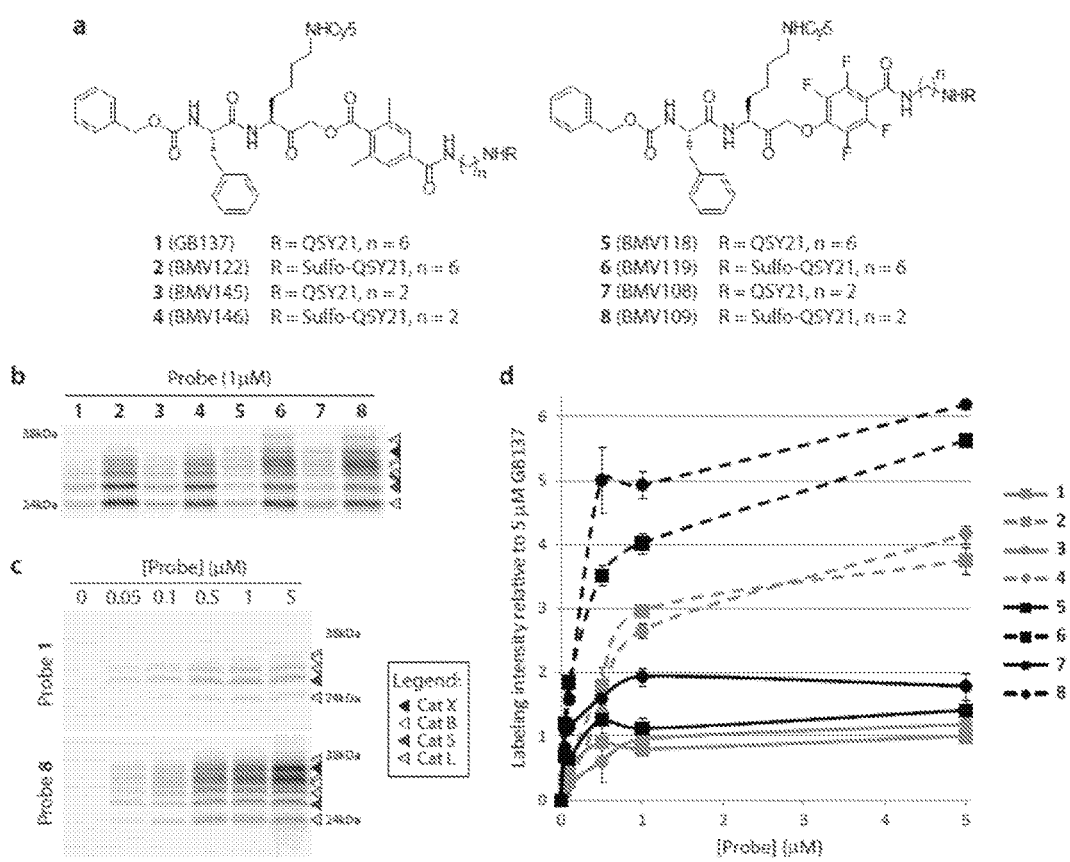
FIG. 1. a) Structures of the qABPs GB 137 (1) and the probes 2-8 synthesized in this work. b) Labeling profile of probes 1-8 in living RAW cells at 1 µM. c) Concentration dependent labeling by probes 1 and 8 in living RAW cells. d) Total cathepsin labeling intensity of probes probes 1-8 in living RAW cells relative to 5 µM GB137 (1).

The cysteine cathepsins are a family of proteases that play important roles in both normal cellular physiology as well as in the pathology of many human diseases. Therefore, a number of substrate and activity based probe (ABP) classes have been developed to study the function of these enzymes. Provided herein is a class of quenched fluorescent activity-based probes containing, in some embodiments, a phenoxymethyl ketone (PMK) electrophile. These reagents show enhanced, broad reactivity towards the cysteine cathepsins resulting in dramatically improved in vitro and in vivo labeling properties compared to previously reported ABPs. The probes are further demonstrated herein to highlight tumors in mice with unprecedented signal intensity and contrast. These new reagents enable the study of cysteine cathepsins on the organismal, tissue, cell and protein level in diverse models of human disease.

Compounds

Accordingly, in some aspects, the instant disclosure provides novel compounds for use in labeling protease enzymes, particularly cathepsins. The compounds of the disclosure may be compounds of the formula (I):

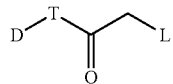
(I)

wherein
L is an ether-linked leaving element;
T is a targeting element; and
D is a detectable element.

The targeting element, T, of the instant compounds may be a peptidic or a non-peptidic structure, and it preferably targets the compound to a cysteine protease.

Non-limiting examples of non-peptidic structural elements usefully incorporated into the instant compounds for these purposes are described in PCT International Publication No. WO2012/118715, which is incorporated herein by reference in its entirety. In preferred embodiments, the non-peptidic targeting element comprises a triazole structure.

Specific examples of compounds of the invention with non-peptidic targeting elements are:

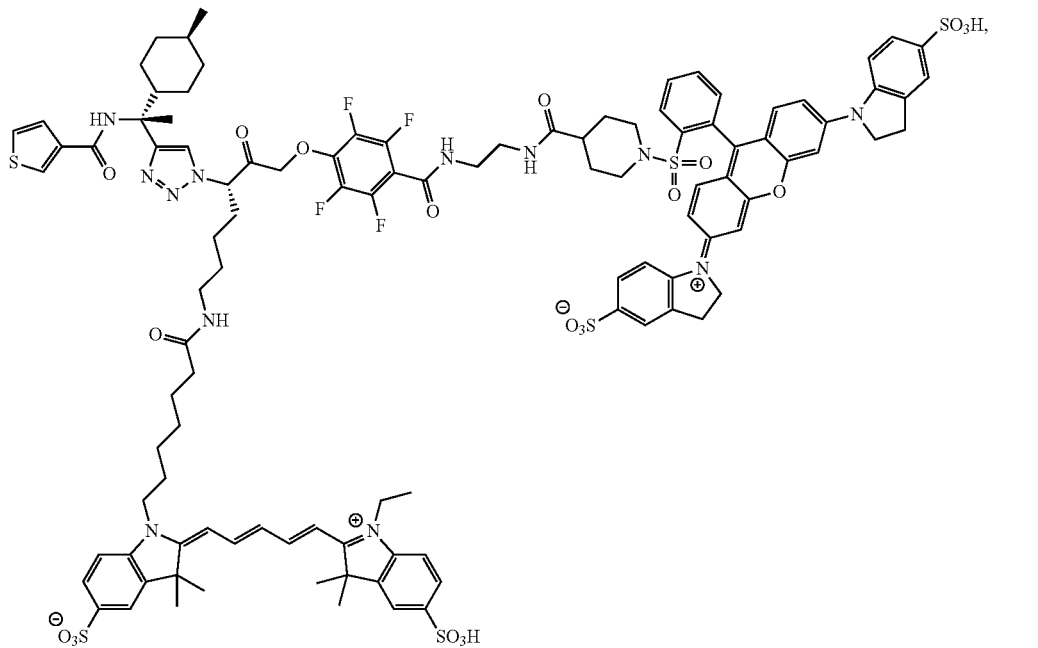

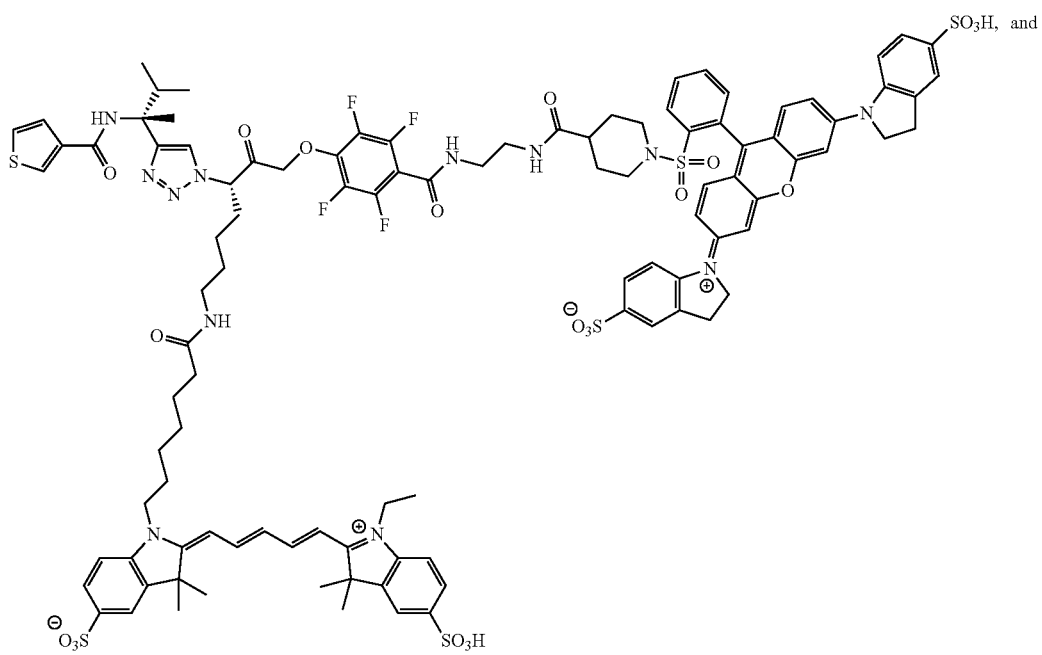

-continued

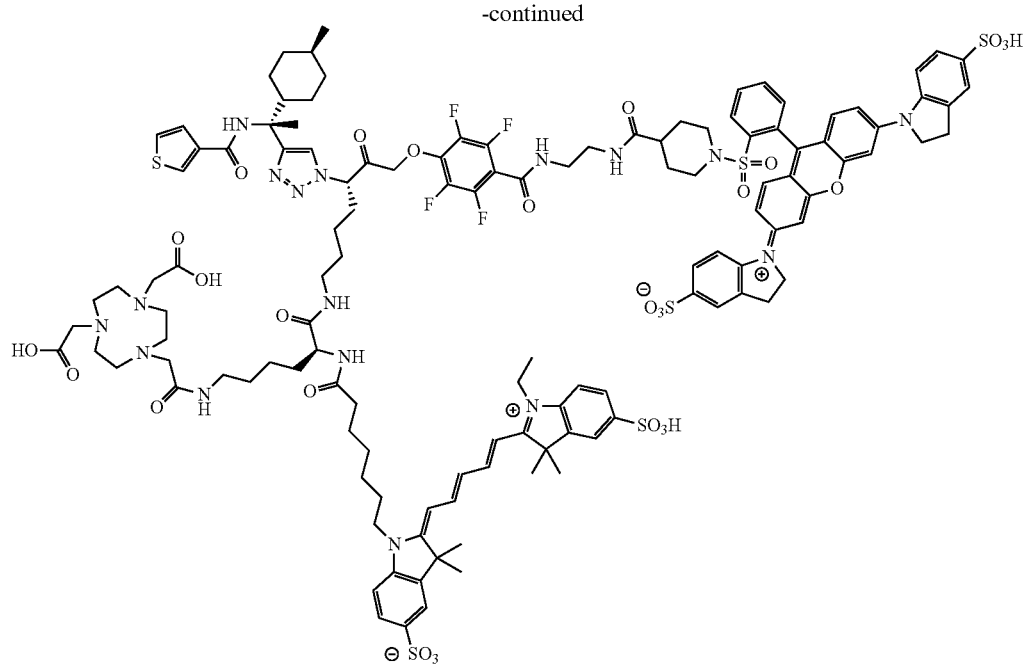

Non-limiting examples of peptidic structural elements that may be usefully incorporated into the instant compounds for targeting the compounds to cysteine proteases, and in particular, cysteine cathepsins, are described in PCT International Publication No. WO2009/124265, which is incorporated herein by reference in its entirety.

In some embodiments of the instant compounds, D-T- is

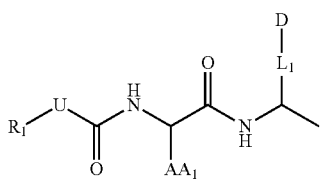

wherein $L_1$ is a linker;
$AA_1$ is an amino acid side chain;
U is O, N, or S;
$R_1$ is alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, or a protecting group, and is optionally substituted with 1 to 3 A groups; and each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamido, or azido.

As used herein, the term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In some embodiments, a straight chain or branched chain alkyl has 30 or fewer carbon atoms in its backbone (e.g., $C_1$-$C_{30}$ for straight chains, $C_3$-$C_{30}$ for branched chains), and more specifically 20 or fewer. Likewise, some cycloalkyls have from 3-10 carbon atoms in their ring structure, and more specifically have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halo, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a thio, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

As used herein, the term "alkoxy" refers to an alkyl group, in certain specific embodiments, a lower alkyl group, having an oxygen attached thereto. Representative alkoxy groups include methoxy, ethoxy, propoxy, t-butoxy, and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed above, except where stability is prohibitive. For example, substitution of alkenyl groups by one or more alkyl, cycloalkyl, heterocyclyl, aryl, or heteroaryl groups is contemplated.

The term "$C_{x-y}$" when used in conjunction with a chemical moiety, such as acyl, acyloxy, alkyl, alkenyl, alkynyl, or alkoxy, is meant to include groups that contain from x to y carbons in the chain. For example, the term "$C_{x-y}$-alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. "$C_0$-alkyl" indicates a hydrogen where the group is in a terminal position, or is a bond if internal. The terms "$C_{2-y}$-alkenyl" and "$C_{2-y}$-alkynyl" refer to substituted or unsubstituted unsaturated aliphatic groups analogous in length and possible substitution to the alkyls described above, but that contain at least one double or triple bond, respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, cycloalkyl, heterocyclyl, aryl, or heteroaryl groups is contemplated.

The term "amide", as used herein, refers to a group

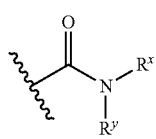

wherein $R^x$ and $R^y$ each independently represent a hydrogen or hydrocarbyl group, or $R^x$ and $R^y$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

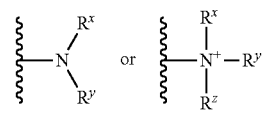

wherein $R^x$, $R^y$, and $R^z$ each independently represent a hydrogen or a hydrocarbyl group, or $R^x$ and $R^y$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein includes substituted or unsubstituted single-ring aromatic groups in which each atom of the ring is carbon. In certain embodiments, the ring is a 5- to 7-membered ring, and in more specific embodiments is a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

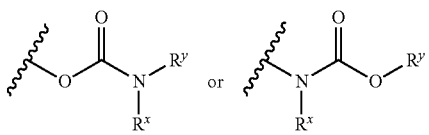

wherein $R^x$ and $R^y$ independently represent hydrogen or a hydrocarbyl group, or $R^x$ and $R^y$ taken together with the atoms to which they are attached complete a heterocycle having from 4 to 8 atoms in the ring structure.

The term "cycloalkyl", as used herein, refers to a non-aromatic saturated or unsaturated ring in which each atom of the ring is carbon. In certain embodiments, a cycloalkyl ring contains from 3 to 10 atoms, and in more specific embodiments from 5 to 7 atoms.

The term "carbonate" is art-recognized and refers to a group —OCO₂—$R^x$, wherein $R^x$ represents a hydrocarbyl group.

The term "carboxy", as used herein, refers to a group represented by the formula —CO₂H.

The term "ester", as used herein, refers to a group —C(O)OR$^x$ wherein $R^x$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "guanidinyl" is art-recognized and may be represented by the general formula

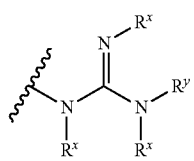

wherein $R^x$ and $R^y$ independently represent hydrogen or a hydrocarbyl.

The terms "halo" and "halogen" as used herein mean halogen and include chloro, fluoro, bromo, and iodo.

The terms "hetaralkyl" and "heteroaralkyl", as used herein, refer to an alkyl group substituted with a hetaryl group.

The terms "heteroaryl" and "hetaryl" include substituted or unsubstituted aromatic single ring structures, in certain specific embodiments 5- to 7-membered rings, more specifically 5- to 6-membered rings, whose ring structures include at least one heteroatom, in some embodiments one to four heteroatoms, and in more specific embodiments one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Typical heteroatoms are nitrogen, oxygen, and sulfur.

The terms "heterocyclyl", "heterocycle", and "heterocyclic" refer to substituted or unsubstituted non-aromatic ring structures, in certain specific embodiments 3- to 10-membered rings, more specifically 3- to 7-membered rings, whose ring structures include at least one heteroatom, in some embodiments one to four heteroatoms, and in more specific embodiments one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes herein, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as acyl, acyloxy, alkyl, alkenyl, alkynyl, or alkoxy is meant to include groups where there are ten or fewer non-hydrogen atoms in the substituent, and in certain embodiments, six or fewer. A "lower alkyl", for example, refers to an alkyl group that contains ten or fewer carbon atoms, and in specific embodiments six or fewer carbon atoms. In certain embodiments, the acyl, acyloxy, alkyl, alkenyl, alkynyl, and alkoxy substituents defined herein are respectively lower acyl, lower acyloxy, lower alkyl, lower alkenyl, lower alkynyl, and lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, more specifically from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc., under conditions in which the compound is to be used. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents may include any substituents described herein, for example, a halogen, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate.

Unless specifically described as "unsubstituted", references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

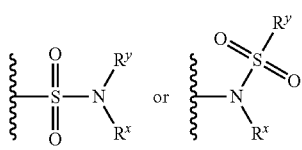

wherein $R^x$ and $R^y$ independently represent hydrogen or hydrocarbyl.

The term "sulfoxide" is art-recognized and refers to the group —S(O)—$R^x$, wherein $R^x$ represents a hydrocarbyl.

The term "sulfo" or "sulfonate" is art-recognized and refers to the group —SO$_3$H, or a pharmaceutically acceptable salt thereof.

The term "sulfone" is art-recognized and refers to the group —S(O)$_2$—$R^x$, wherein $R^x$ represents a hydrocarbyl.

The term "thioalkyl", as used herein, refers to an alkyl group substituted with a thiol group.

The term "thioester", as used herein, refers to a group —C(O)S$R^x$ or —SC(O)$R^x$ wherein IV represents a hydrocarbyl.

The term "thioether", as used herein, is equivalent to an ether, wherein the oxygen is replaced with a sulfur.

The term "urea" is art-recognized and may be represented by the general formula

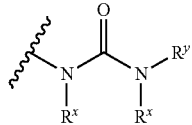

wherein $R^x$ and $R^y$ independently represent hydrogen or a hydrocarbyl.

The compounds of the instant invention are generally synthesized using standard synthetic chemical techniques, for example using the methods described in the Example section below. Other useful synthetic techniques are described, for example, in *March's Advanced Organic Chemistry: Reactions, Mechanisms, and Structure, 7th Ed.*, (Wiley, 2013); Carey and Sundberg, *Advanced Organic Chemistry 4$^{th}$ Ed., Vols. A and B* (Plenum 2000, 2001); *Fiesers' Reagents for Organic Synthesis, Volumes 1-27* (Wiley, 2013); *Rodd's Chemistry of Carbon Compounds, Volumes 1-5 and Supplementals* (Elsevier Science Publishers, 1989); *Organic Reactions, Volumes 1-81* (Wiley, 2013); and *Larock's Comprehensive Organic Transformations* (VCH Publishers Inc., 1989) (all of which are incorporated by reference in their entirety). The compounds are normally synthesized using starting materials that are generally available from commercial sources or are readily prepared using methods well known to those skilled in the art. See, e.g., *Fiesers' Reagents for Organic Synthesis, Volumes 1-27* (Wiley, 2013), or *Beilsteins Handbuch der organischen Chemie, 4, Aufl.* ed. Springer-Verlag, Berlin, including supplements.

When referring to components of the compounds of the invention, the term "residue derived from" may be used to describe a residue formed by the reaction of a first reactive functional group on a first component and a second reactive functional group on a second component to form a covalent bond. In exemplary embodiments, an amine group on a first component may be reacted with an activated carboxyl group on a second component to form a residue including one or more amide moieties. Other permutations of first and second reactive functional groups are encompassed by the invention. For example, the copper-catalyzed or copper-free reaction of an azide-substituted first component with an alkyne-substituted second component results in a triazole-containing residue through the well-known "click" reaction, as would be understood by those of ordinary skill in the art. See Kolb et al. (2001) *Angew. Chem. Int. Ed. Engl.* 40:2004; Evans (2007) *Aus. J. Chem.* 60:384. Exemplary methods of generating non-peptidic fluorescent imaging probes using "click" reactions are provided in PCT International Publication No. WO 2012/118715. Adaptation of these methods to generate or modify compounds of the instant claims is within the skill in the art.

One of ordinary skill in the art would understand that a protecting group is reversibly attached to a desired position of the molecule to control the reaction of other agents at that position. Protecting groups useful in the practice of the instant invention are well known in the art. See, for example, *Greene's Protective Groups in Organic Synthesis, 4$^{th}$ edition*, by P. G. M. Wuts and T. W. Greene (Wiley-Interscience, 2006); and *Protecting Groups*, by P. Kocienski (Thieme, 2005).

The $L_1$ group of the instant compounds is a linker group that connects the detectable element, D, to the targeting element. This group may be any suitable linker, as would be understood by the person of ordinary skill in the art. The $L_1$ group is preferably an alkyl linker group, wherein the alkyl linker is optionally substituted, and furthermore, wherein the carbons in the linker are optionally replaced by heteroatoms to the extent that the resulting structure is chemically stable. Such substitutions and replacements should be understood to include intervening groups within the linker such as ethers, thioethers, disulfides, esters, amides, carbonates, carbamates, and so forth. Preferred linkers range in length from 5 to 40 bonds and may be branched, straight-chain, or contain rings. Linkers may in some cases include double bonds. They may be hydrophobic or hydrophilic as so desired according to the particular requirements.

It should further be understood that the connection between the $L_1$ group and the detectable element, D, may be any suitable chemical connection, as would be understood by the skilled artisan. For example, the instant compounds may in some cases be conveniently prepared by including in the detectable element precursor a moiety that is reactive with a particular chemical group, such as, for example, an amino group, a thiol group, or the like. The detectable element can in such a situation be readily attached to the targeting element through the reaction of this group on the targeting element. These types of attachments are thus understood to be within the scope of the disclosed compounds, even if the structural details of the connection are not explicitly shown.

The $AA_1$ group of the instant compounds may be any natural or unnatural amino acid side chain as would be understood by the skilled artisan. In preferred embodiments, the $AA_1$ group is an aralkyl amino acid side chain that is optionally substituted with 1 to 3 A groups. In even more preferred embodiments, the $AA_1$ group is a phenylalanine side chain.

In preferred compounds, the U group is O.

The detectable element of the instant compounds is in specific embodiments a fluorescent label, a radiolabel, a chelator, or the like. Examples of radiolabels and chelators suitable for use in these compounds are described in PCT International Publication No. 2009/124265.

In preferred embodiments of the instant compounds, the detectable element is a fluorescent label. As is known by those of ordinary skill in the art, fluorescent labels emit electromagnetic radiation, preferably visible light, when stimulated by the absorption of incident electromagnetic radiation. A wide variety of fluorescent labels, including labels having reactive moieties useful for coupling the label to reactive groups such as, for example amino groups, thiol groups, and the like, are commercially available. See, e.g., *The Molecular Probes® Handbook—A Guide to Fluorescent Probes and Labeling Technologies.*

An example of a fluorescent label is fluorescein, which is widely used in immunofluorescence labeling. Fluorescein is a xanthene dye with an absorption maximum at 495 nanometers. A related fluorophore is Oregon Green, a fluorinated derivative of fluorescein.

The fluorescent label used in the detectable element of the compounds of the instant invention may in some embodiments be a pH-dependent fluorophore. Such fluorescent labels, for example as used in the compounds labeled "LES12" and "LES13", shown below, display a fluorescence spectrum that depends on the pH of the label's environment, as would be understood by the skilled artisan, and may therefore be useful in reporting information about the environment of the label following reaction, for example information about the location of or type of protease labeled by the reactive compound. The pH-dependent fluorescence of various labels usefully included in the detectable element of the instant compounds is well known. See, e.g., *The Molecular Probes® Handbook—A Guide to Fluorescent Probes and Labeling Technologies*, which is hereby incorporated by reference in its entirety.

Other exemplary fluorescent labels suitable for use in the instant compounds are bora-diaza-indecene, rhodamine, and cyanine dyes. In particular, bora-diaza-indecene dyes are represented by 4,4-difluoro-4-bora-3a,4a-diaza-s-indacene, known as the BODIPY® dyes. Various derivatives of these dyes are known and are considered suitable for use as a detectable element in the compounds of the instant disclosure. See, e.g., Chen et al. (2000) *J. Org. Chem.* 65:2900-2906.

Another class of fluorescent label usefully employed in the compounds of the instant invention are the IRDye infrared dyes available from Li-Cor (www.licor.com). Non-limiting examples of these dyes are IRDye 800CW, IRDye 680RD, IRDye 680LT, IRDye 750, IRDye 700DX, IRDye 800RS, and IRDye 650.

Rhodamine dyes are a class of dyes based on the rhodamine ring structure. Rhodamines include, inter alia, tetramethylrhodamine (TMR), a very common fluorophore for preparing protein conjugates, especially antibody and avidin conjugates, and carboxy tetramethyl-rhodamine (TAMRA), a dye commonly used for oligonucleotide labeling and automated nucleic acid sequencing. Rhodamines are established as natural supplements to fluorescein-based fluorophores, which offer longer wavelength emission maxima and thus open opportunities for multicolor labeling or staining.

Also included within the group of rhodamine dyes are the sulfonated rhodamine series of fluorophores known as Alexa Fluor dyes. The dramatic advances in modern fluorophore technology are exemplified by the Alexa Fluor dyes, which were introduced by Molecular Probes. These sulfonated rhodamine derivatives exhibit higher quantum yields for more intense fluorescence emission than spectrally similar probes, and have several additional improved features, including enhanced photostability, absorption spectra matched to common laser lines, pH insensitivity, and a high degree of water solubility.

The cyanine dyes correspond to a family of related dyes, Cy2, Cy3, Cy5, Cy7, and their derivatives, that are based on the partially saturated indole nitrogen heterocyclic nucleus with two aromatic units being connected via a polyalkene bridge of varying carbon number. These probes exhibit fluorescence excitation and emission profiles that are similar to many of the traditional dyes, such as fluorescein and tetramethylrhodamine, but with enhanced water solubility, photostability, and higher quantum yields. Most of the cyanine dyes are more environmentally stable than their traditional counterparts, rendering their fluorescence emission intensity less sensitive to pH and organic mounting media. In a manner similar to the Alexa Fluors, the excitation wavelengths of the Cy series of synthetic dyes are tuned specifically for use with common laser and arc-discharge sources, and the fluorescence emission can be detected with traditional filter combinations. The cyanine dyes are readily available as reactive dyes or fluorophores. The cyanine dyes generally have broader absorption spectra than members of the Alexa Fluor family, making them somewhat more versatile in the choice of laser excitation sources for confocal microscopy.

In preferred embodiments, the detectable element of the instant compounds is the cyanine dye, Cy5.

In some embodiments, it may be beneficial to include multiple fluorescent labels, radiolabels, chelators, or the like, within the detectable element of the compounds of the invention. For example, the exemplary compounds labeled "LES12" and "LES13" below include two different fluorescent labels within a single detectable element. Such multiple labeling can be achieved using routine coupling chemistry as would be understood by the skilled artisan. For example, the fluorescent labels in the "LES12" and "LES13" compounds were coupled using "click" chemistry. An example of an intermediate compound useful in the synthesis of compounds containing multiple labels within the detectable element by "click" chemistry is shown below ("WL938"). This compound contains an azido group and can thus be readily reacted with a suitable alkyne-containing reagent in a "click" reaction. The positions of the alkyne and azido groups could also be reversed, if desired, as would be understood by those of ordinary skill in the art.

In some embodiments, the compound of the invention is a compound of formula (I), wherein T is a peptidic targeting element, and the compound is further described in the following numbered sentences:

1. A compound of formula (I), wherein D-T- is a short detectable peptidic group; and
   L is an ether-linked leaving element.
2. The compound of sentence 1, wherein the detectable peptidic group contains 1 to 4 amino acid residues.
3. The compound of sentence 2, wherein D-T is:

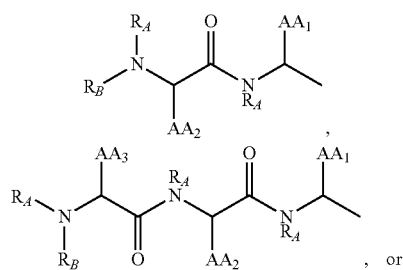

, or

-continued

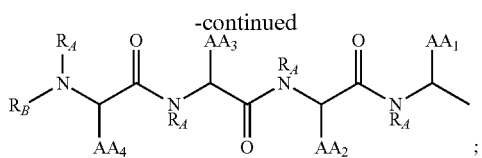

wherein each $AA_1$, $AA_2$, $AA_3$, and $AA_4$ is independently an amino acid side chain or -$L_1$-D;

each $R_A$ is independently hydrogen or $R_1$;

$R_B$ is hydrogen, $R_1$, —C(O)$R_1$, —C(O)O$R_1$, —C(O)S$R_1$, or —C(O)N($R_1$)($R_A$);

$R_1$ is alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, a protecting group, or -$L_1$-D, and is optionally substituted with 1 to 3 A groups;

each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamido, or azido; and $L_1$ is a linker.

4. The compound of sentence 3, wherein each $R_A$ is hydrogen; and $R_B$ is —C(O)O$R_1$.

5. The compound of sentence 3, wherein D-T- is

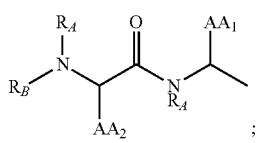

each $AA_1$ and $AA_2$ is independently an amino acid side chain or -$L_1$-D; and each $R_A$ is hydrogen.

6. The compound of sentence 3, wherein D-T- is

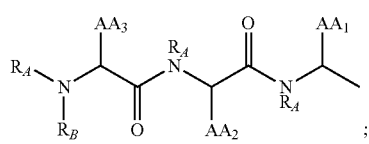

each $AA_1$, $AA_2$, and $AA_3$ is independently an amino acid side chain or -$L_1$-D; and each $R_A$ is hydrogen.

7. The compound of sentence 3, wherein D-T is

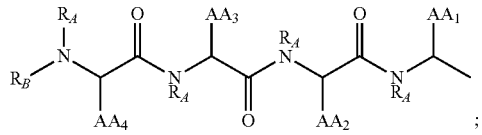

each $AA_1$, $AA_2$, $AA_3$, and $AA_4$ is independently an amino acid side chain or -$L_1$-D; and each $R_A$ is hydrogen.

8. The compound of sentence 3, wherein $L_1$ is an optionally substituted alkyl linker, wherein each carbon atom is optionally replaced with a heteroatom.

9. The compound of sentence 3, wherein $R_B$ is —C(O)O$R_1$.

10. The compound of sentence 3, wherein D is a fluorescent label, a radiolabel, or a chelator.

11. The compound of sentence 10, wherein D is a fluorescent label.

12. The compound of sentence 11, wherein the fluorescent label is a fluorescein, an Oregon green, a bora-diazaindecene, a rhodamine, or a cyanine label.

13. The compound of sentence 12, wherein the fluorescent label is a cyanine label.

14. The compound of sentence 13, wherein the cyanine label is Cy5.

The $AA_1$, $AA_2$, $AA_3$, and $AA_4$ groups in these embodiments of the instant compounds may be independently any natural or unnatural amino acid side chain as would be understood by the skilled artisan, or the group "-$L_1$-D". In preferred embodiments, the group is an aralkyl amino acid side chain that is optionally substituted with 1 to 3 A groups. In even more preferred embodiments, the group is a side chain from phenylalanine. In other preferred embodiments, the group is a side chain from an acidic amino acid residue, such as a side chain from an aspartic acid or glutamic acid residue, or a side chain from an alkyl amino acid residue, such as an alanine, leucine, isoleucine, valine, or other such amino acid residue, in any combination. Side chains from other amino acid residues, such as lysine, arginine, tyrosine, glutamine, asparagine, and the like, are also preferred in the instant compounds.

In compound embodiments where the $AA_1$, $AA_2$, $AA_3$, or $AA_4$ group is an "-$L_1$-D" group, the $L_1$ linker component may be provided by an amino acid side chain. For example, a lysine residue conveniently provides an amino-alkyl group for reaction with a suitably activated detectable element.

A "short" detectable peptidic group is defined herein as a detectable peptidic group having up to 10 amino acid residues.

The ether-linked leaving element, L, of the instant compounds influences the reactivity of the compounds with their target enzyme active site and may also affect the specificity of targeting to a particular enzyme. The ether linkage of the leaving element in these compounds is in contrast to the ester linkage of other activity based probes, such as the acyloxymethyl ketones (AOMKs). An ether-linked leaving element, such as, for example, a phenol ether-linked leaving element, may provide improved stability in vivo over ester-linked or other types of probes.

In some embodiments, the ether-linked leaving element of the instant compounds comprises a quencher. The term "quencher" refers to a chemical entity that modulates the emission of a fluorophore. In some cases, a quencher may itself be a fluorescent molecule that emits fluorescence at a characteristic wavelength distinct from the label whose fluorescence it is quenching. Thus, a fluorophore may act as a quencher when appropriately coupled to another dye and vice versa. In these situations, the increase in fluorescence from the acceptor molecule, which is of a different wavelength to that of the donor label, may separately report interactions of the labeled compound with its environment, such as, for example, the active site of a target enzyme. In some cases, the quencher does not itself fluoresce (i.e., the quencher is a "dark acceptor"). Such quenchers include, for example, dabcyl, methyl red, the QSY diarylrhodamine dyes, and the like. In particular, dabcyl (4-dimethylaminophenylazo)benzoic acid) is a common dark quencher used widely in many assays, such as "molecular beacons" for DNA detection. U.S. Pat. No. 5,989,823. Diazo dyes of the BHQ series, which are referred to as "Black Hole Quenchers", provide a broad range of absorption which overlaps well with the emission of many fluorophores. PCT International Publication No. WO01/86001. The QSY series dyes from Molecular Probes is another example of dark quencher dyes that have been used extensively as quenching reagents in many bioassays. U.S. Pat. No. 6,399,392.

QSY 7 in particular is a nonfluorescent diarylrhodamine derivative. U.S. Patent Application Publication No. 2005/0014160. QSY21 is a nonfluorescent diarylrhodamine chromophore with strong absorption in the visible spectrum, and is an effective fluorescence quencher. Fluorophore/quencher pairs are further illustrated in U.S. Patent Application Publication No. 2004/0241679.

IRDye QC-1 (available from Li-Cor) is another example of a nonfluorescent dye that is suitable for use as a quencher in the instant compounds. It efficiently quenches fluorescence from a wide range of fluorophores, including those ranging in wavelength from the visible region to the near-infrared.

In some embodiments of the instant compounds, the leaving group element, L, is $L_2$-$L_3$-Q, wherein $L_2$ is a phenoxy group, $L_3$ is a linker, and Q is a quencher. The leaving group element may be, for example,

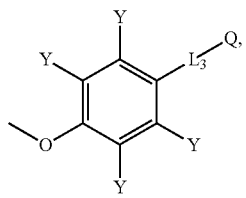

wherein each Y is independently an electron-withdrawing group or hydrogen. In such compounds, each Y may independently be a halogen or hydrogen. In specific compounds, the L group is, for example,

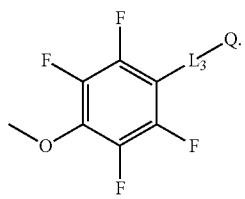

The $L_3$ linker group of the above-described leaving element may be any suitable linker, as would be understood by the person of ordinary skill in the art. In particular, the $L_3$ linker group may be, for example, an $L_1$ group, as described above.

In other specific compounds, the L group is, for example,

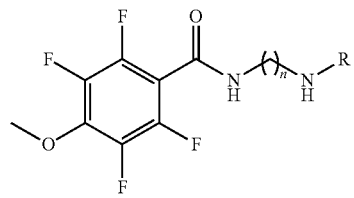

wherein R is a QSY quencher and n is an integer from 1 to 8. In specific embodiments, the QSY quencher is a hydrophilic quencher, such as, for example, a sulfo-QSY quencher.

In some specific embodiments, the compounds of the instant disclosure have the structure of formula (II):

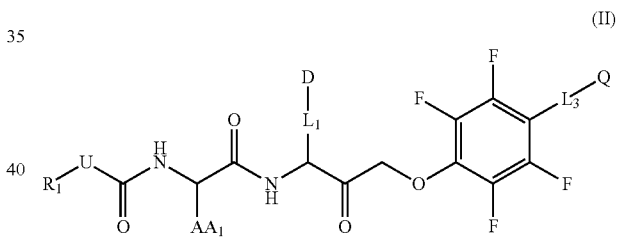

In some more specific embodiments, the compounds of the instant disclosure have the structure of formula (III):

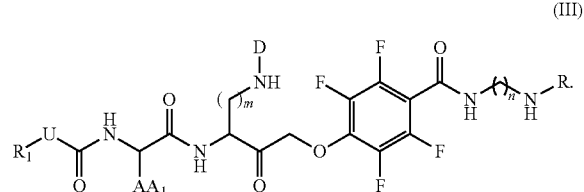

In these embodiments, m and n are independently integers from 1 to 16.

In some embodiments, R is QSY21 or sulfo-QSY21, and D is Cy5.

Specific non-limiting compound embodiments of the invention include:

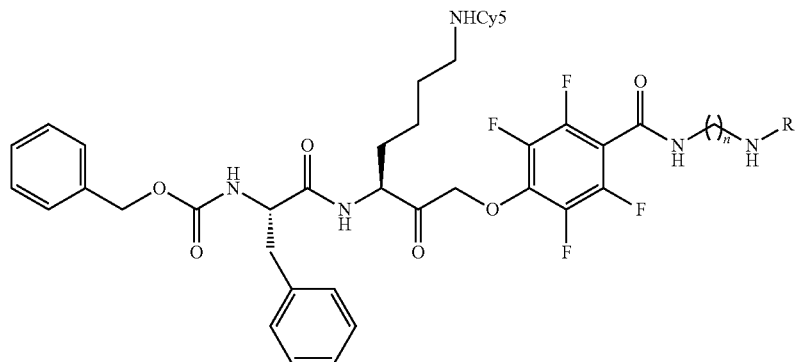

where
R=QSY21 and n=6;
R=Sulfo-QSY21 and n=6;
R=QSY21 and n=2; and
R=Sulfo-QSY21 and n=2.

In some embodiments, the compound of the invention is a compound having the structure of formula (IV):

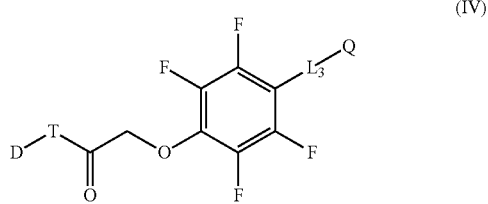

wherein T is a peptidic targeting element, and the compound is further described in the following numbered sentences:

1. A compound of formula (IV), wherein D-T- is a short detectable peptidic group;
   $L_3$ is a linker; and
   Q is a quencher.
2. The compound of sentence 1, wherein the detectable peptidic group contains 1 to 4 amino acid residues.
3. The compound of sentence 2, wherein D-T is:

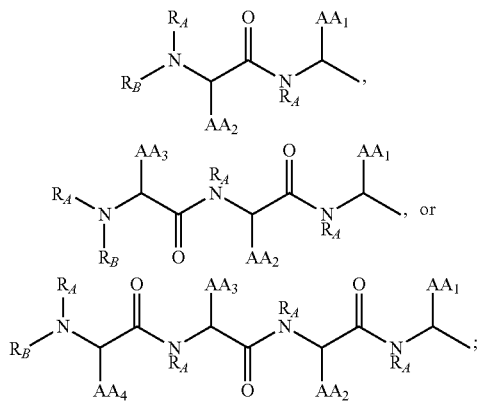

wherein
each $AA_1$, $AA_2$, $AA_3$, and $AA_4$ is independently an amino acid side chain or -$L_1$-D;
each $R_A$ is independently hydrogen or $R_1$;

$R_B$ is hydrogen, $R_1$, —C(O)$R_1$, —C(O)O$R_1$, —C(O)S$R_1$, or —C(O)N($R_1$)($R_A$);
$R_1$ is alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, a protecting group, or -$L_1$-D, and is optionally substituted with 1 to 3 A groups;
each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamido, or azido; and
$L_1$ is a linker.
4. The compound of sentence 3, wherein
   each $R_A$ is hydrogen; and
   $R_B$ is —C(O)O$R_1$.
5. The compound of sentence 3, wherein D-T- is

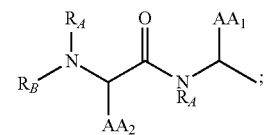

each $AA_1$ and $AA_2$ is independently an amino acid side chain or -$L_1$-D; and
each $R_A$ is hydrogen.
6. The compound of sentence 3, wherein D-T- is

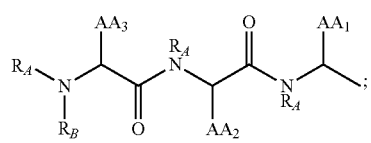

each $AA_1$, $AA_2$, and $AA_3$ is independently an amino acid side chain or -$L_1$-D; and
each $R_A$ is hydrogen.

7. The compound of sentence 3, wherein D-T is

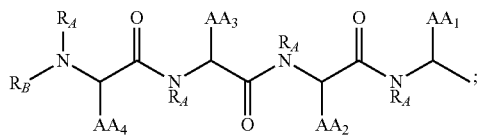

each $AA_1$, $AA_2$, $AA_3$, and $AA_4$ is independently an amino acid side chain or $-L_1$-D; and
each $R_A$ is hydrogen.
8. The compound of sentence 3, wherein $L_1$ is an optionally substituted alkyl linker, wherein each carbon atom is optionally replaced with a heteroatom.
9. The compound of sentence 3, wherein $R_B$ is —C(O)$OR_1$.
10. The compound of sentence 3, wherein D is a fluorescent label, a radiolabel, or a chelator.
11. The compound of sentence 10, wherein D is a fluorescent label.
12. The compound of sentence 11, wherein the fluorescent label is a fluorescein, an Oregon green, a bora-diaza-indecene, a rhodamine, or a cyanine label.
13. The compound of sentence 12, wherein the fluorescent label is a cyanine label.
14. The compound of sentence 13, wherein the cyanine label is Cy5.

The $AA_1$, $AA_2$, $AA_3$, and $AA_4$ groups in these embodiments of the instant compounds may be independently any natural or unnatural amino acid side chain as would be understood by the skilled artisan, or the group "-$L_1$-D". In preferred embodiments, the group is an aralkyl amino acid side chain that is optionally substituted with 1 to 3 A groups. In even more preferred embodiments, the group is a side chain from phenylalanine. In other preferred embodiments, the group is a side chain from an acidic amino acid residue, such as a side chain from an aspartic acid or glutamic acid residue, or a side chain from an alkyl amino acid residue, such as an alanine, leucine, isoleucine, valine, or other such amino acid residue, in any combination. Side chains from other amino acid residues, such as lysine, arginine, tyrosine, glutamine, asparagine, and the like, are also preferred in the instant compounds.

In compound embodiments where the $AA_1$, $AA_2$, $AA_3$, or $AA_4$ group is an "-$L_1$-D" group, the $L_1$ linker component may be provided by an amino acid side chain. For example, a lysine residue conveniently provides an amino-alkyl group for reaction with a suitably activated detectable element.

A "short" detectable peptidic group is defined herein as a detectable peptidic group having up to 10 amino acid residues.

Other specific non-limiting compound embodiments of the invention include:

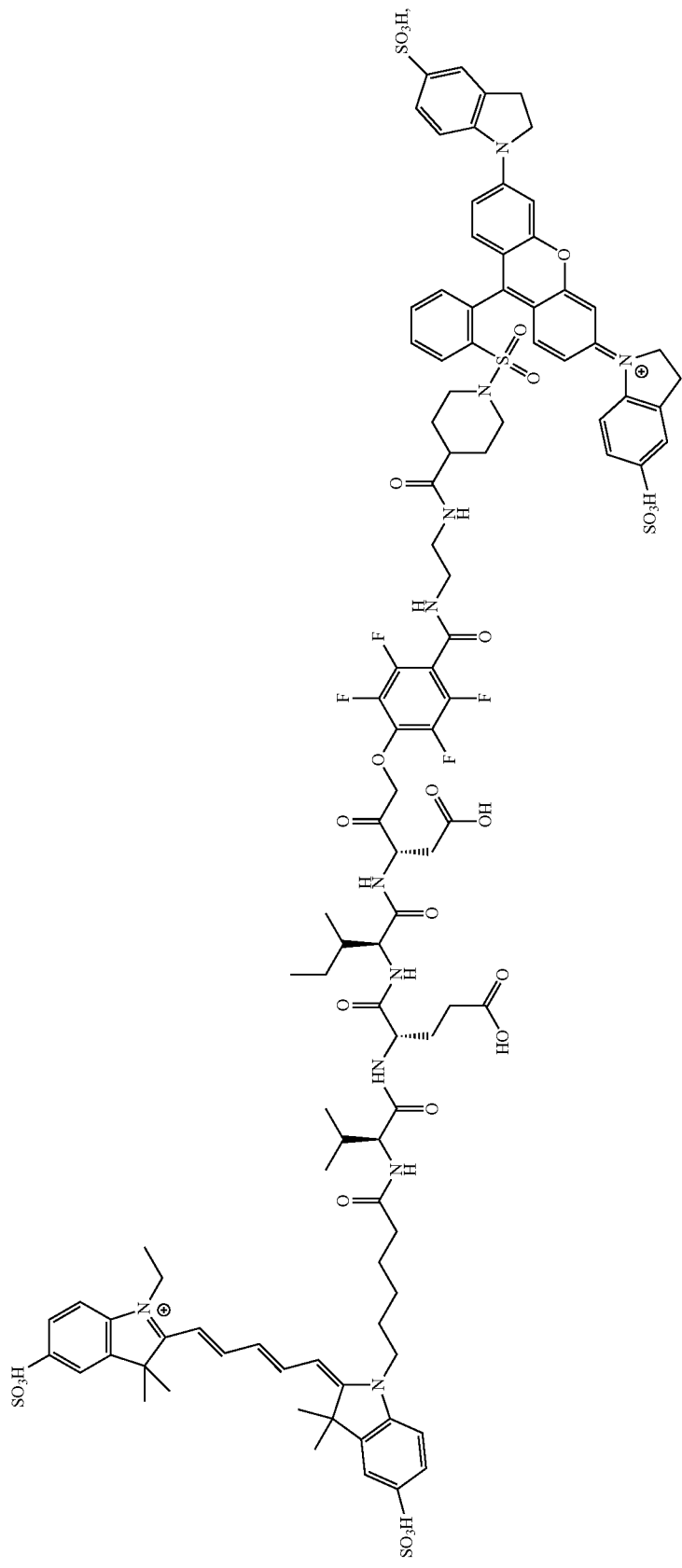

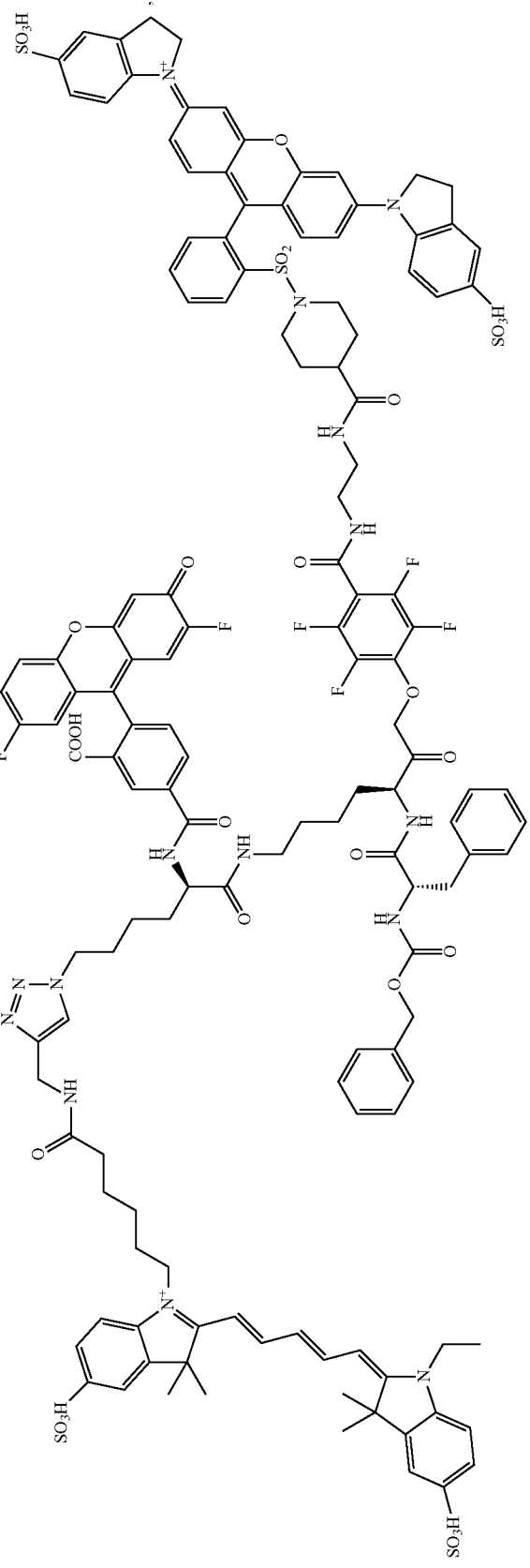

-continued
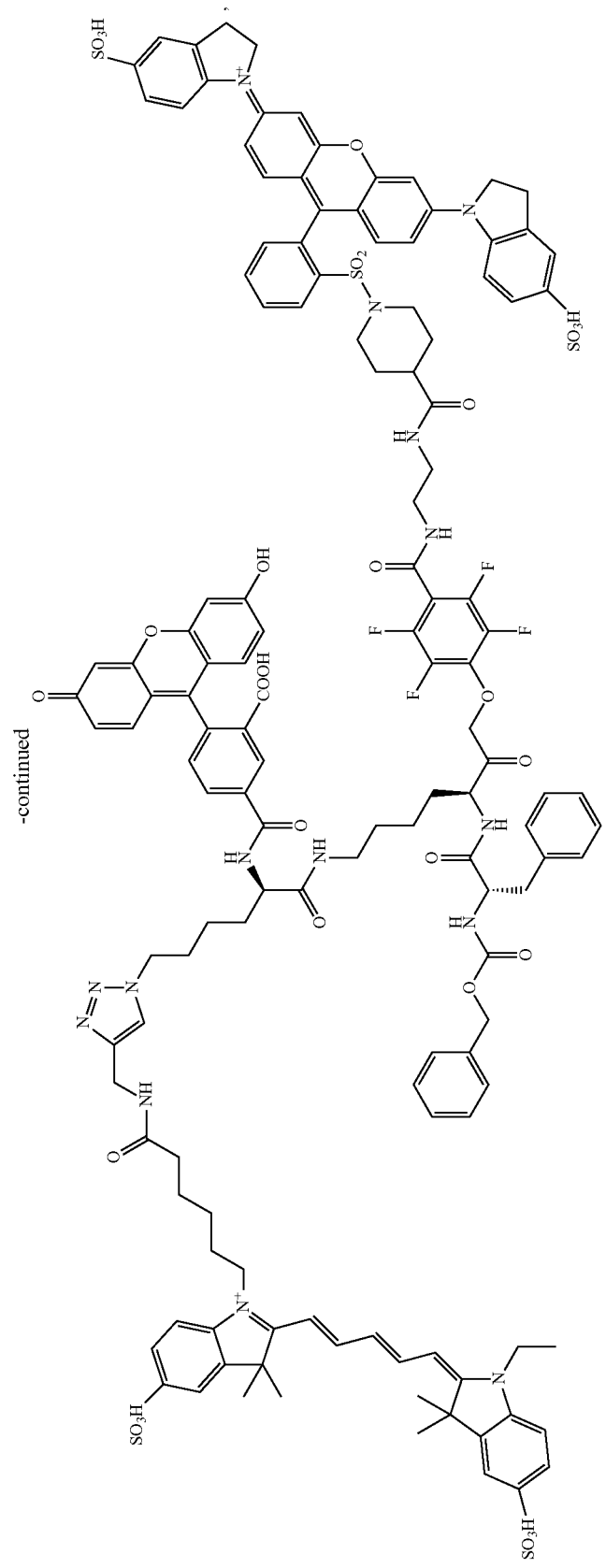
LES13

-continued
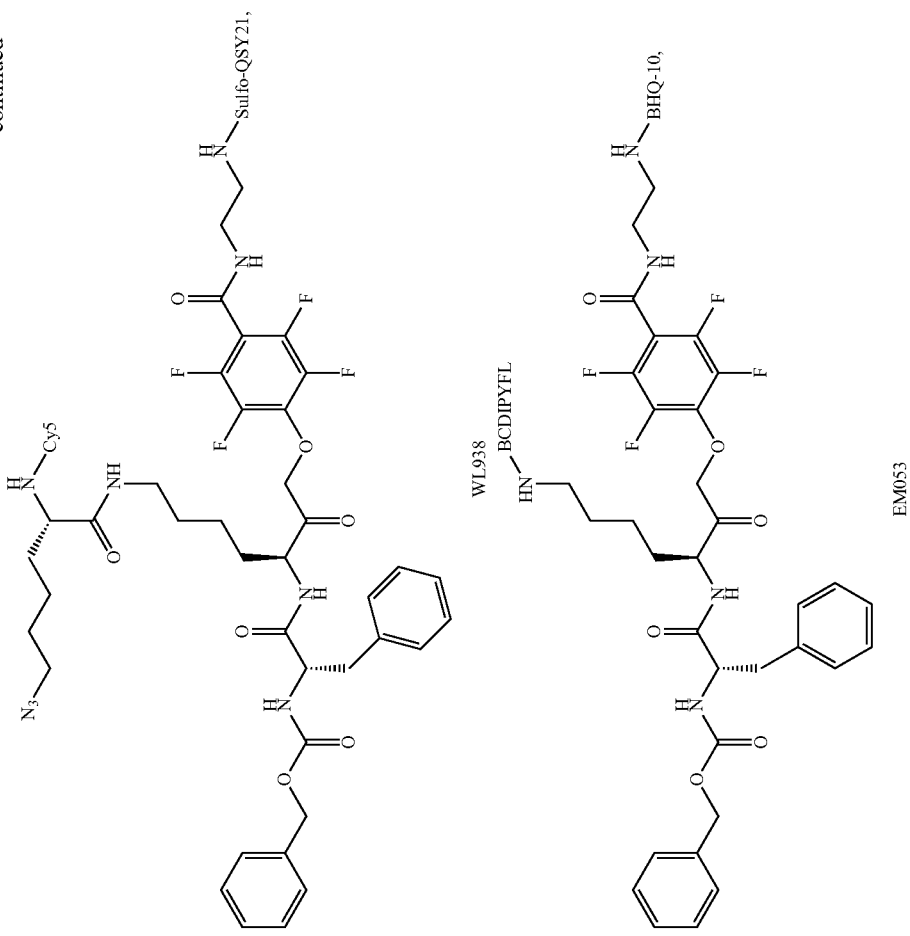

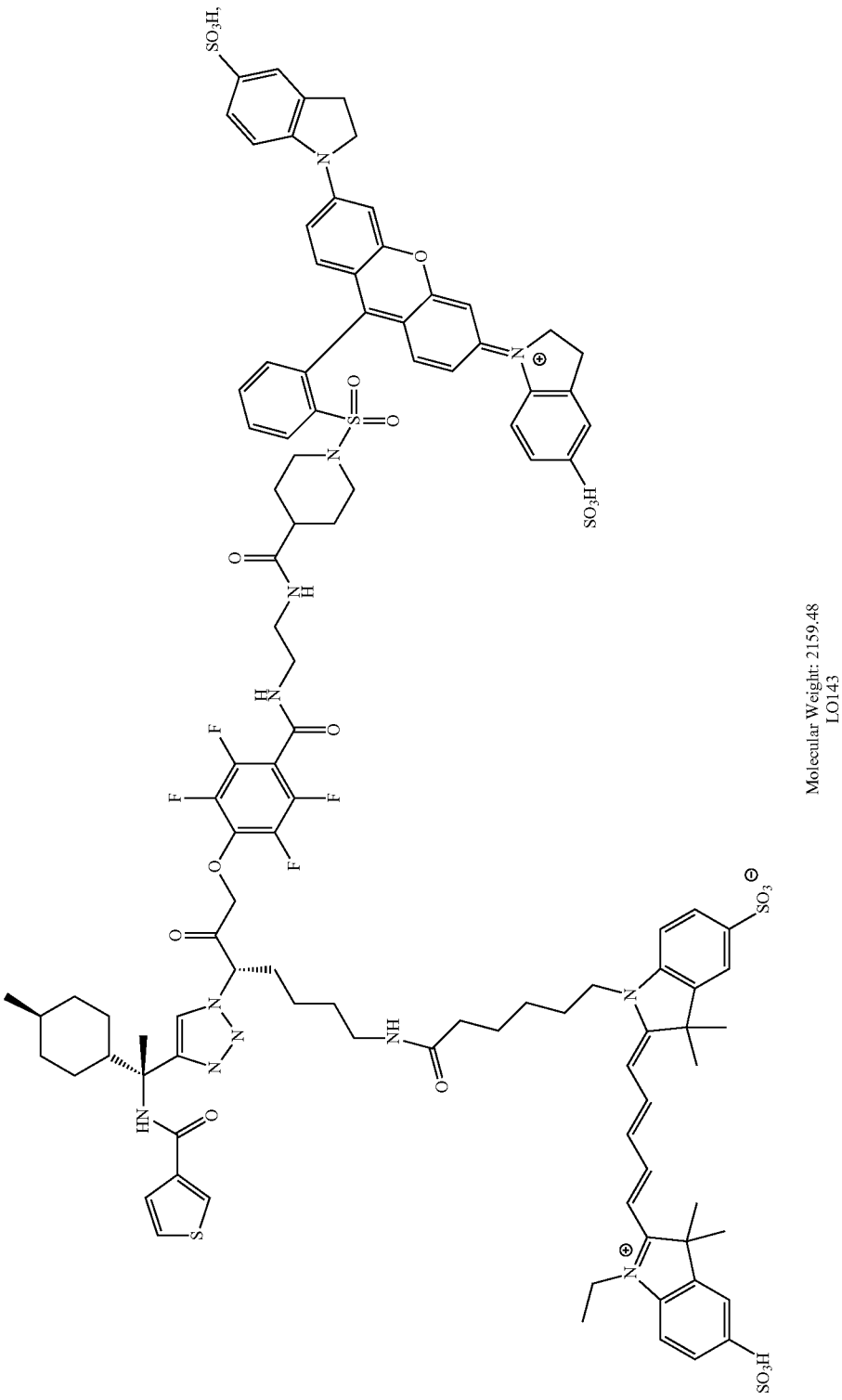
Molecular Weight: 2159.48
LO143

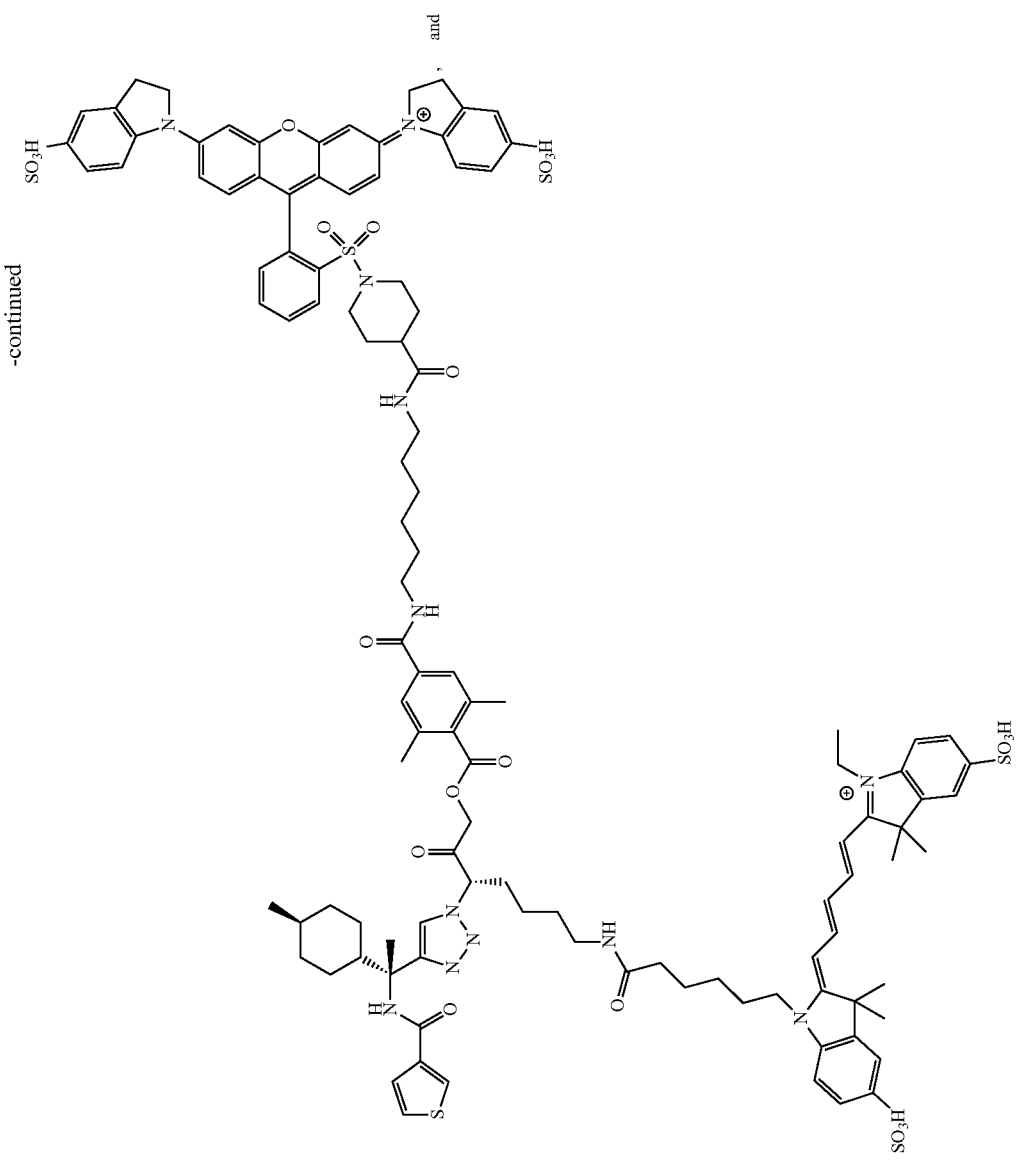

-continued
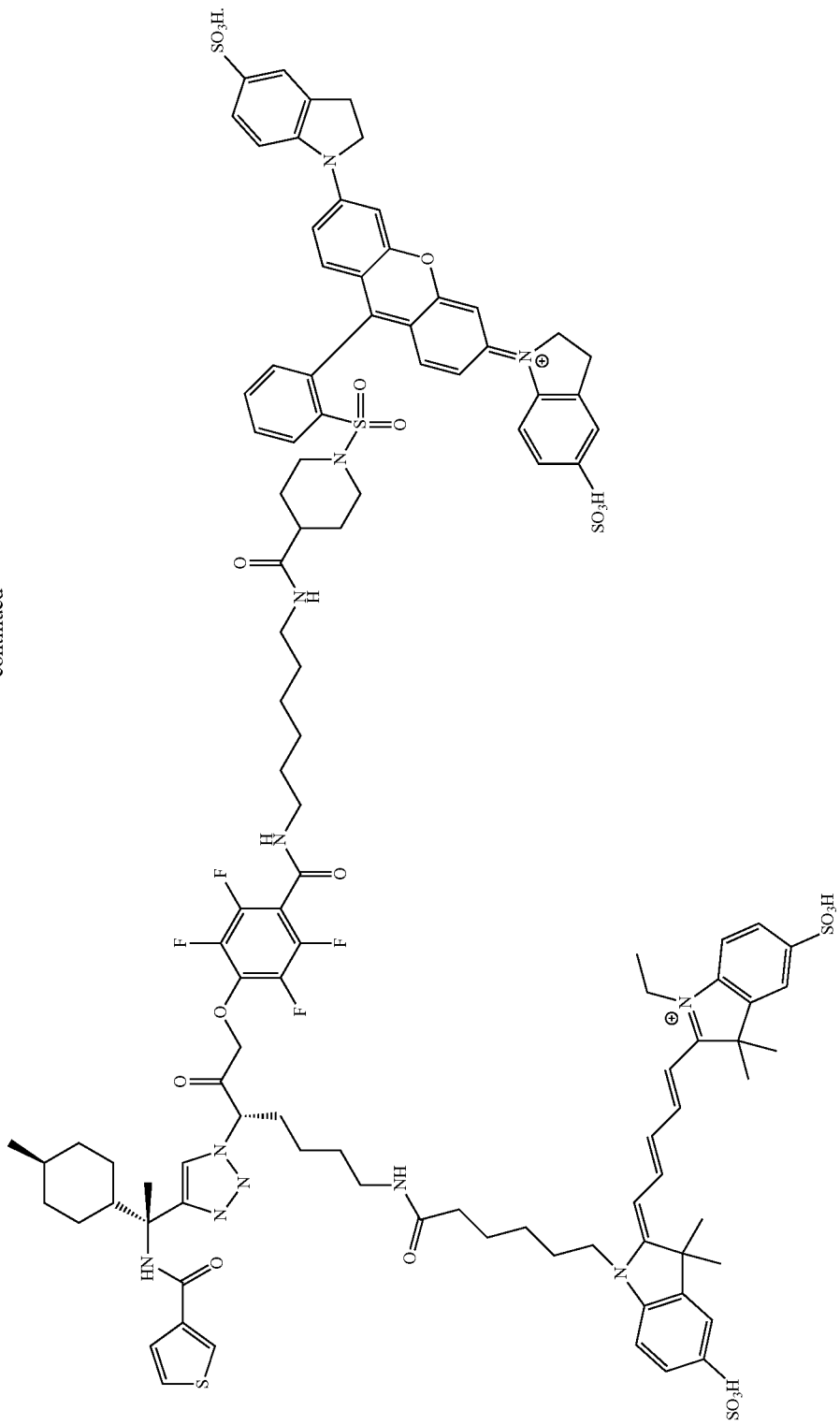
Molecular Weight: 2216.60
LO219

Pharmaceutical Compositions

In another aspect, the instant invention provides pharmaceutical compositions comprising a compound of the invention and a pharmaceutically acceptable carrier. Such compositions are useful, for example, in the imaging of tissues in an animal and are further useful in assessing the activity of enzymes in the animal, for example, protease enzymes. In particular, for compounds of the invention that label cathepsins, the pharmaceutical compositions may usefully serve as tools for the non-invasive optical imaging of cancer cells.

Pharmaceutically acceptable carriers are well known in the art and include, for example, aqueous solutions such as water or physiologically buffered saline or other solvents or vehicles such as glycols, glycerol, oils such as olive oil or injectable organic esters. In a specific embodiment, when such pharmaceutical compositions are for human administration, the aqueous solution is pyrogen free, or substantially pyrogen free. The excipients may be chosen, for example, to effect delayed release of an agent or to selectively target one or more cells, tissues or organs. The pharmaceutical composition may be in dosage unit form such as tablet, capsule, sprinkle capsule, granule, powder, syrup, suppository, injection or the like. The composition may also be present in a transdermal delivery system, e.g., a skin patch.

A pharmaceutically acceptable carrier may contain physiologically acceptable agents that act, for example, to stabilize or to increase the absorption of a compound of the instant invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition also may comprise a liposome or other polymer matrix, which may have incorporated therein, for example, a compound of the invention. Liposomes, for example, which consist of phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent, or encapsulating material, involved in carrying or transporting the subject compounds from one organ, or portion of the body, to another organ, or portion of the body. Each carrier must be "acceptable" in the sense of being compatible with the other ingredients of the formulation and not injurious to the patient. Some examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. See *Remington: The Science and Practice of Pharmacy,* 20th ed. (Alfonso R. Gennaro ed.), 2000.

A pharmaceutical composition containing a compound of the instant invention may be administered to a subject by any of a number of routes of administration including, for example, orally (for example, drenches as in aqueous or non-aqueous solutions or suspensions, tablets, boluses, powders, granules, pastes for application to the tongue); sublingually; anally, rectally, or vaginally (for example, as a pessary, cream, or foam); parenterally (including intramuscularly, intravenously, subcutaneously, or intrathecally as, for example, a sterile solution or suspension); nasally; intraperitoneally; subcutaneously; transdermally (for example as a patch applied to the skin); or topically (for example, as a cream, ointment or spray applied to the skin). The compound may also be formulated for inhalation. In certain embodiments, a compound of the instant invention may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4,172,896, as well as in patents cited therein.

Methods of Labeling and Visualizing

In another aspect, the invention provides methods of visualizing a tumor in an animal, comprising the step of administering a composition of the invention to the animal.

In yet another aspect, the invention provides methods of visualizing a tumor in an animal, comprising the steps of administering a composition of the invention to the animal, and measuring a detectable signal generated in the animal from a reaction of the composition with a cathepsin cysteine protease, wherein the detectable signal is associated with a tumor in the animal.

In some embodiments of the methods, the detectable signal is a fluorescent signal. In some embodiments, the fluorescent signal is generated at a tumor margin.

The administration of peptide imaging agents to an animal is well understood by those of ordinary skill in the art. In preferred embodiments, the agent is administered by injection, although any other suitable means of administration is considered within the scope of the invention.

The methods of the invention are directed at the labeling and visualization of a protease, in particular a cysteine protease, in an animal. Suitable animals include animals expressing cysteine proteases, particularly in tumor cells. In preferred embodiments, the animal is a mammal. In highly preferred embodiments, the animal is a human. In other preferred embodiments, the animal is a livestock animal or a pet.

In some embodiments, the methods of the invention comprise the step of measuring a detectable signal generated in the animal. Methods of measuring the detectable signal include, but are not limited to, imaging methods, for example fluorescent imaging methods. In some embodiments, the fluorescent imaging system is, for example, a Xenogen IVIS 100 system, but any suitable imaging system may be used.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Example, which is included herewith for purposes of illustration only and is not intended to be limiting of the invention.

EXAMPLE

Synthesis and Characterization of Quenched Fluorescent Cysteine Cathepsin Imaging Probes Containing a Novel Phenoxymethyl Ketone (PMK) Electrophile The goal of this work was to develop a qABP with overall improved in vivo properties compared to the existing qABPs that could be used for non-invasive optical imaging of cancer. It was therefore decided to optimize three major elements of the probe, the quencher, the linker and the electrophilic "warhead". One of the biggest drawbacks of the cysteine cathepsin qABPs reported to date is the relatively poor aqueous solubility. Sulfonate groups were therefore introduced to the QSY21 quencher (Xing et al. (2005) *J. Am. Chem. Soc.* 127:4158-9) in order to improve the water solubility and thereby the bio-distribution of the probe. The length of the spacer tethering the electrophile and the quencher was also varied in order to decrease the lipophilicity of the qABP. Finally, a new electrophile was explored in order to increase the range of possible cathepsin targets. Since several members of the cysteine cathepsin family are upregulated in a variety of cancers (Mohamed & Sloane (2006) *Nat. Rev. Cancer* (2006) 6:764-75), a brighter fluorescence signal in tumors would be expected if the probe targets a broad spectrum of cysteine cathepsin activities. In order to obtain a more pan-reactive probe, the size of the electrophile was decreased, and the reactivity was increased. It has previously been shown that the 2,3,5,6-tetrafluoro substituted phenoxymethyl ketone (PMK) electrophile has a greater reactivity for cysteine dipeptidyl aminopeptidases compared to the 2,6-dimethylbenzoic acid derived acyloxymethyl ketone (AOMK). Deu et al. (2010) Chem Biol. 17:808-819. The smaller size of the PMK could also increase the pan-reactivity since the binding grooves of some of the cysteine cathepsins, are sterically restricted. Blum et al. (2005) *Nat. Chem. Biol.* 1:203-9; Blum et al. (2007) *Nat. Chem. Biol.* 3:668-77; Paulick & Bogyo (2011) *ACS Chem. Biol.* 6:563-72. Furthermore, the phenol ether is expected to be more stable in vivo compared to the AOMK electrophile which contains an ester linkage that can be degraded by estereases.

Figure 4:
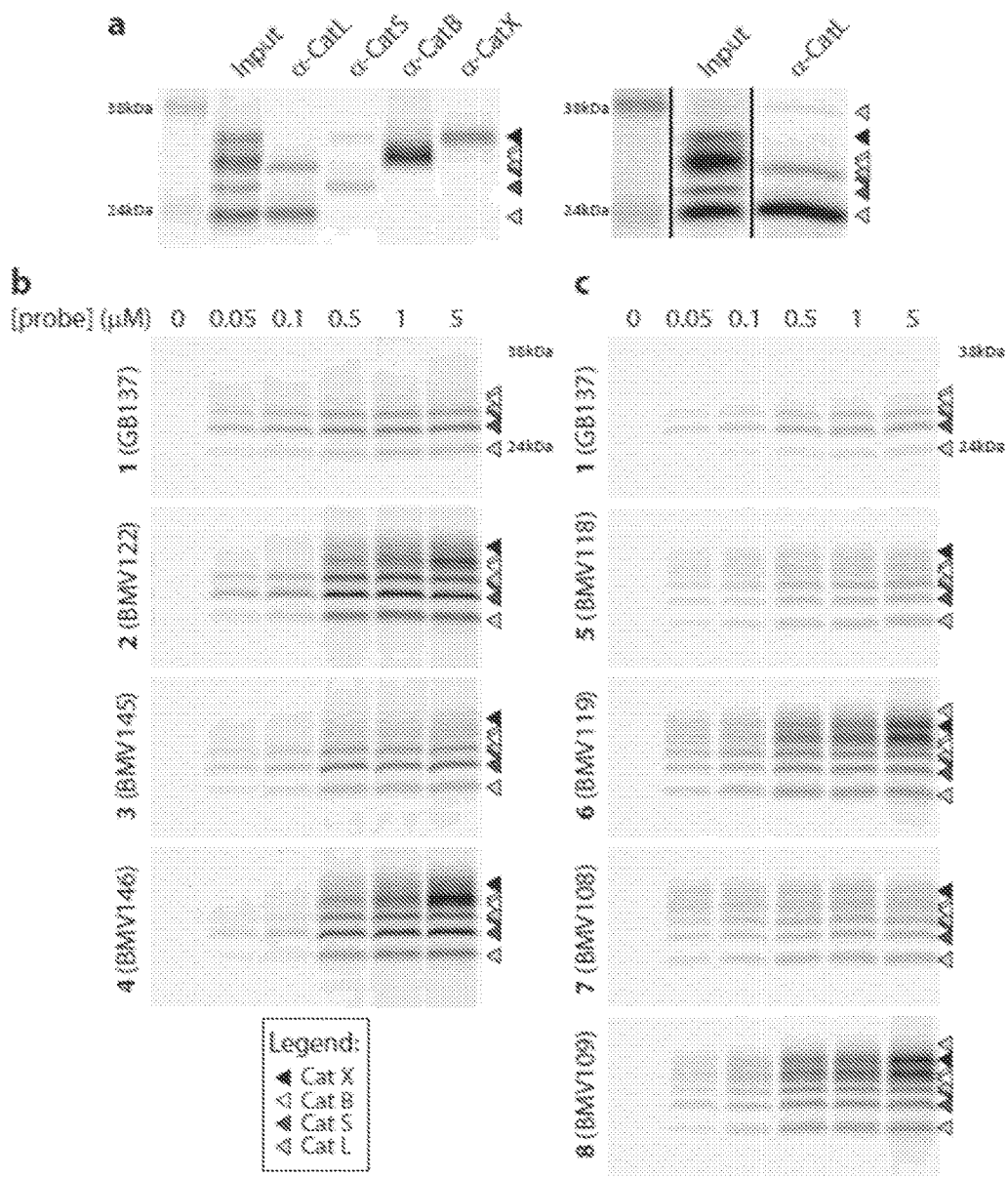
FIG. 4. a) Immunoprecipitation of BMV 109 labeled cysteine cathepsins. b,c) Concentration dependent labeling by probes 1-8 in living RAW cells. The panels in b) and c) were run on the same gels respectively.

As a starting point for this study 7 analogs (2-8) of qABP GB 137 (1) were synthesized. Blum et al. (2007) *Nat. Chem. Biol.* 3:668-77. (FIG. 1a) These compounds represent all combinations of the two electrophiles, two quenchers and two linker lengths. All probes were synthesized using an optimized, solution chemistry based procedure as described in the description associated with Scheme 1 below. The specificity and potency of the probe were initially tested by labeling intact RAW 264.7 cells (Mouse leukaemic monocyte macrophage cell line) (FIG. 1b). Several trends were observed in the properties of the probes. All of the Sulfo-QSY21 functionalized qABPs (2, 4, 6 and 8) showed stronger overall cathepsin labeling compared to the more hydrophobic QSY21 containing probes (1, 3, 5 and 7). Interestingly, the change in the spacer length from a hexyl to an ethyl linker did not have a dramatic influence on the labeling profile. Perhaps the most striking observation was that the qABPs with the PMK electrophile showed a broader cysteine cathepsin labeling profile compared to their AOMK counterparts. Probes 5-8 showed robust cathepsin X labeling and Sulfo-QSY21 functionalized probes 6 and 8 were able to label a higher molecular weight pro-form of cathepsin L. The identities of the fluorescently labeled cathepsins were determined by immunoprecipitation (FIG. 4a). Upon performing titration labeling experiments in live RAW cells, several other interesting trends were observed (FIG. 1c,d. FIG. 4b,c). The most hydrophobic qABPs (1 and 5) reach a reduced maximum of labeling intensity at 0.5 µM, suggesting that their reduced water solubility results in precipitation of the probes at the higher concentrations. The shorter spacer length seems to be beneficial, with all probes carrying the ethyl spacer giving brighter labeling compared to their hexyl containing counterparts. When comparing the AOMKs with the PMKs, a clear difference in selectivity is observed. The AOMK qABPs preferentially label cathepsins S and L and only at higher concentrations label cathepsin B. Surprisingly, the AOMK qABPs 2-4 label cathepsin X, even though prior studies had shown that several other related AOMKs are incapable of labeling this target (Paulick & Bogyo (2011) *ACS Chem. Biol.* 6:563-72). The PMK qABPs also labeled all target cysteine cathepsins with equal intensity, even at the lower probe concentrations. Together, these experiments demonstrate that increased hydrophilicity improves labeling intensity and that the novel PMK qABPs have a broader, more pan-cysteine cathepsin labeling profile.

Figure 2:
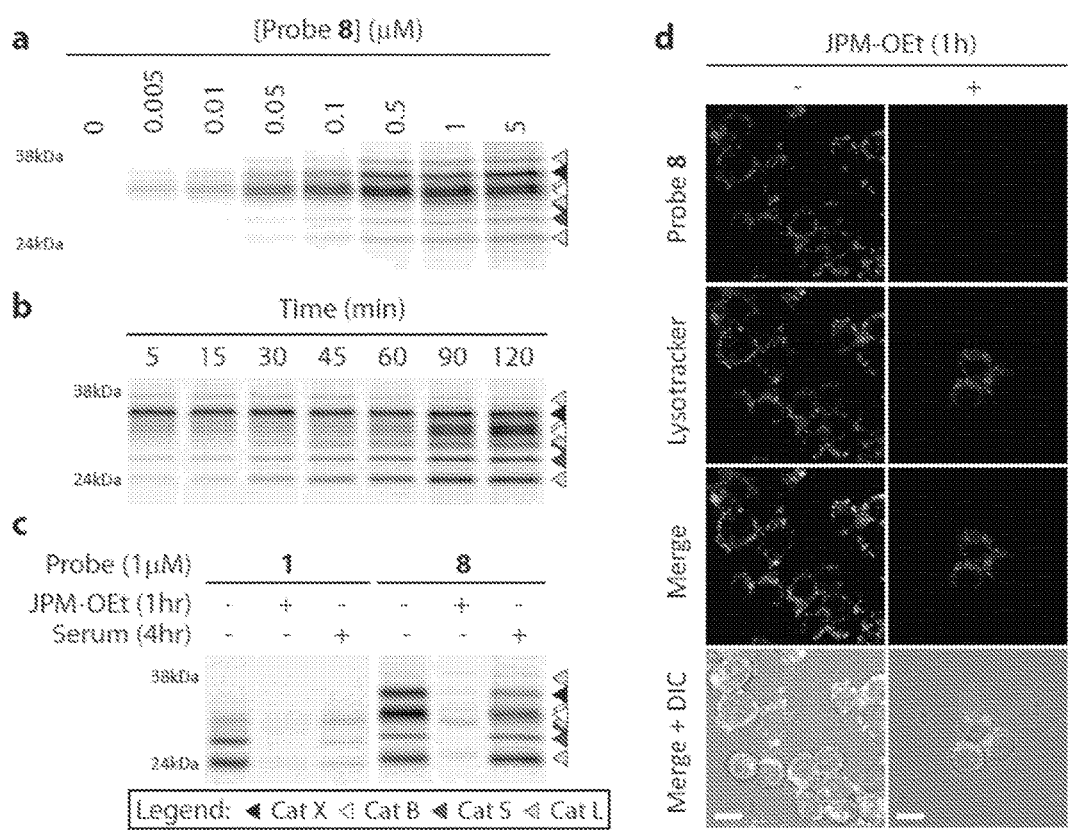
FIG. 2. a) Concentration dependent labeling of RAW cell lysate by probe 8 at pH 5.5. b) Labeling time course with 0.5 µM probe 8 in living RAW cells. c) Inhibition of labeling of probes 1 and 8 in living RAW cells by pretreatment with JPM-OEt (50 µM) and serum stability. d) Live cell fluorescence microscopy of RAW cells exposed to 1 µM probe 8 (top row of panels) and colocalization with lysotracker (second row of panels, scale bar 10 µm).

Because the PMK qABP 8 was the most optimal in terms of overall labeling intensity and broad cathepsin reactivity, it was decided to proceed with this probe for further in vivo studies. To further define the target selectivity, RAW cell lysates were labeled with increasing concentrations of qABP 8 at pH 5.5. These results demonstrated that the probe is most potent towards cathepsins B and X with labeling observed at concentrations as low as 5 nM. However, labeling of all of the cathepsins (B, S, L, X) was saturated by 500 nM of the probe (FIG. 2a). When the probe was used for a timecourse labeling of live RAW cells at the set concentration of 500 nM, a rapid saturation of cathepsin X was observed, and then a more slow labeling of cathepsin S, L and B with cathepsin B labeling signal increasing even at 120 min (FIG. 2b). These data indicate that the probe is likely able to access pools of cathepsin X most rapidly, perhaps due to its localization within or on the surface of the cells. It also indicates that cathepsins B and X may be in alternate locations in the cells which can be accessed by the probe to different extents. In order to test the stability of the new PMK probe, the effects of serum exposure on labeling in RAW cells were examined (FIG. 1c). Whereas 4 hours of serum pre-exposure to the original AOMK probe 1 resulted in a loss of nearly 70% of target labeling, more than 80% of the labeling was retained for PMK qABP 8. Pre-treatment of the cells with the cysteine cathepsin inhibitor JPM-OEt also blocked more than 90% of this labeling. Given the stability and improved labeling properties of the PMK probe, live cell fluorescence microscopy studies were next performed. These results confirmed that the probe produced bright and specific labeling signals and that the majority of the probe labeled cathepsins reside in lysosomes (FIG. 2d).

Figure 3:
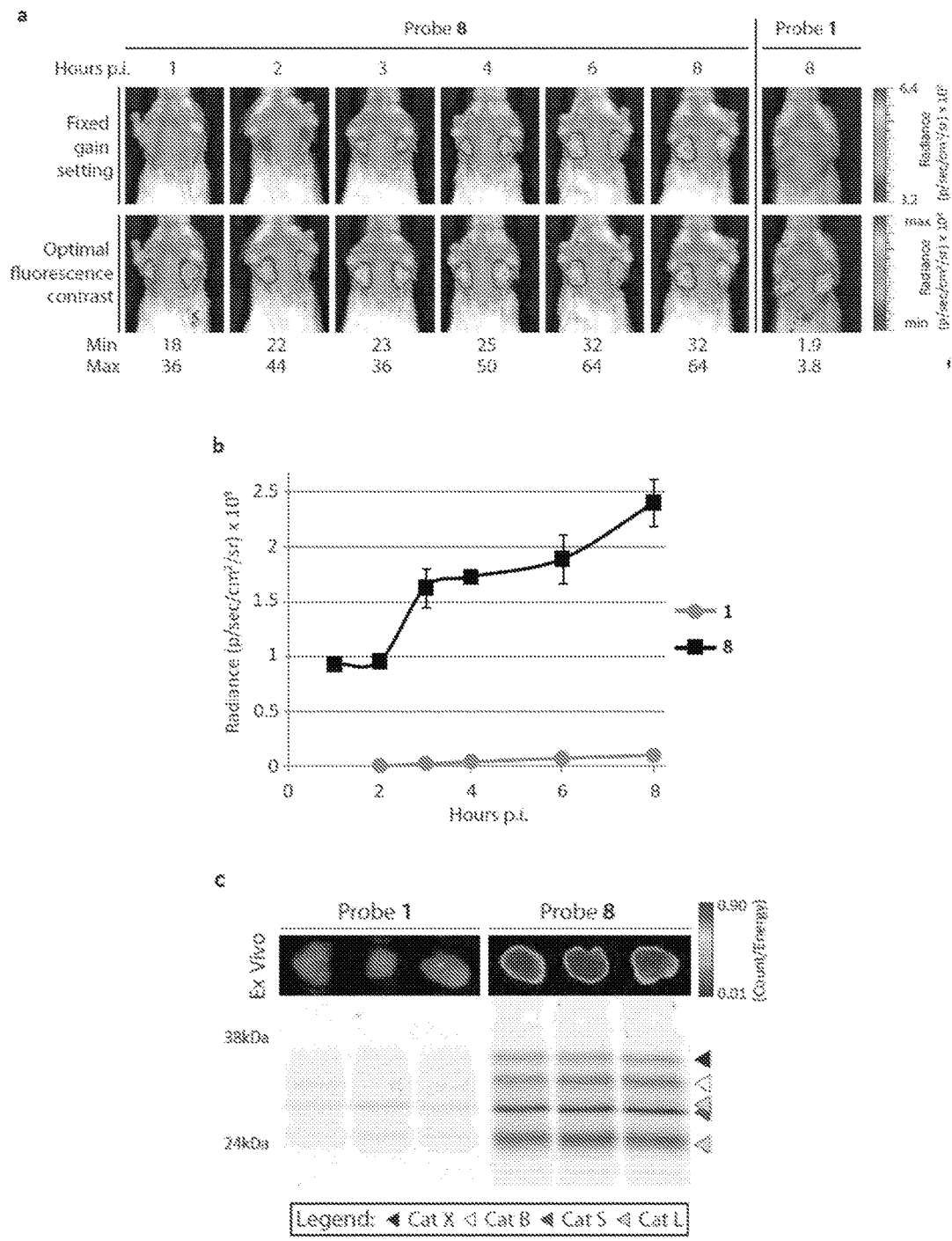
FIG. 3. a) Non-invasive optical imaging time-course of tumor bearing mice injected with probe 8 and 1 (right panels). The lower panels represent the optimal fluorescence contrast at each time point. b) Time-dependent tumor-specific fluorescence (tumor—background) for mice treated with probe 1 or 8 (n=3; data represent mean values±standard errors). c) Ex vivo tumor fluorescence (top panel) and in vivo fluorescently labeled proteins after SDS-PAGE visualized by in-gel fluorescence scanning (lower panel). d) Fluorescence intensity at end point of noninvasive optical imaging (shown in a), ex vivo tumor imaging, and in-gel fluorescence labeling (shown in c). Intensity relative to probe 1 is depicted (n=3; data represent mean values±standard errors). e) Fluorescence microscopy of probe 8 (left panel) treated tumor tissue section with CD68 immuno-staining (middle panel) and nuclear staining (DAPI—right panel, scale bar 50 µm). f) 3D reconstruction of CLSM of probe 8 (Red) treated tumor tissue section with CD68 immuno-staining (Green) and nuclear staining (DAPI—Blue).
Figure 3:
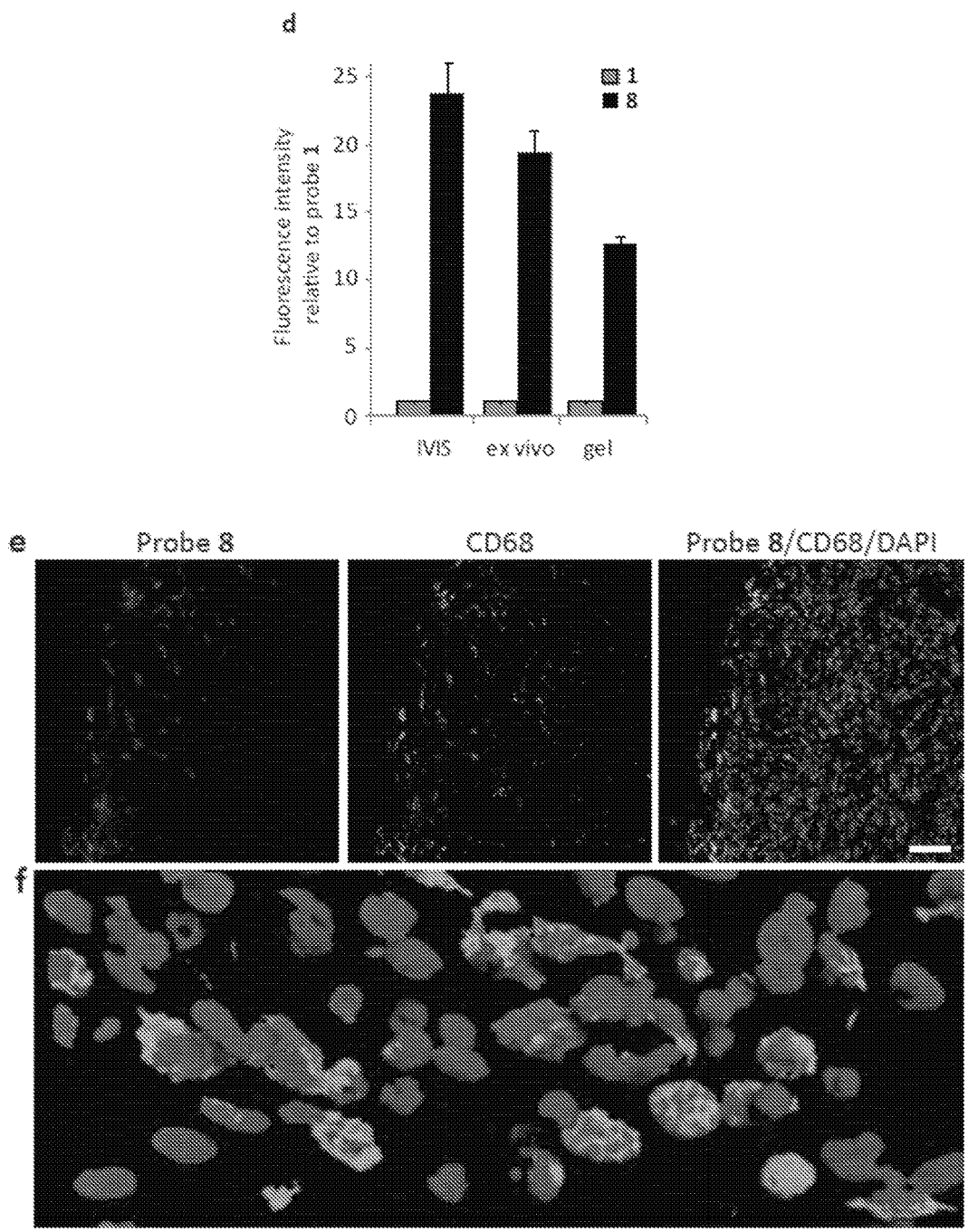
Figure 5:
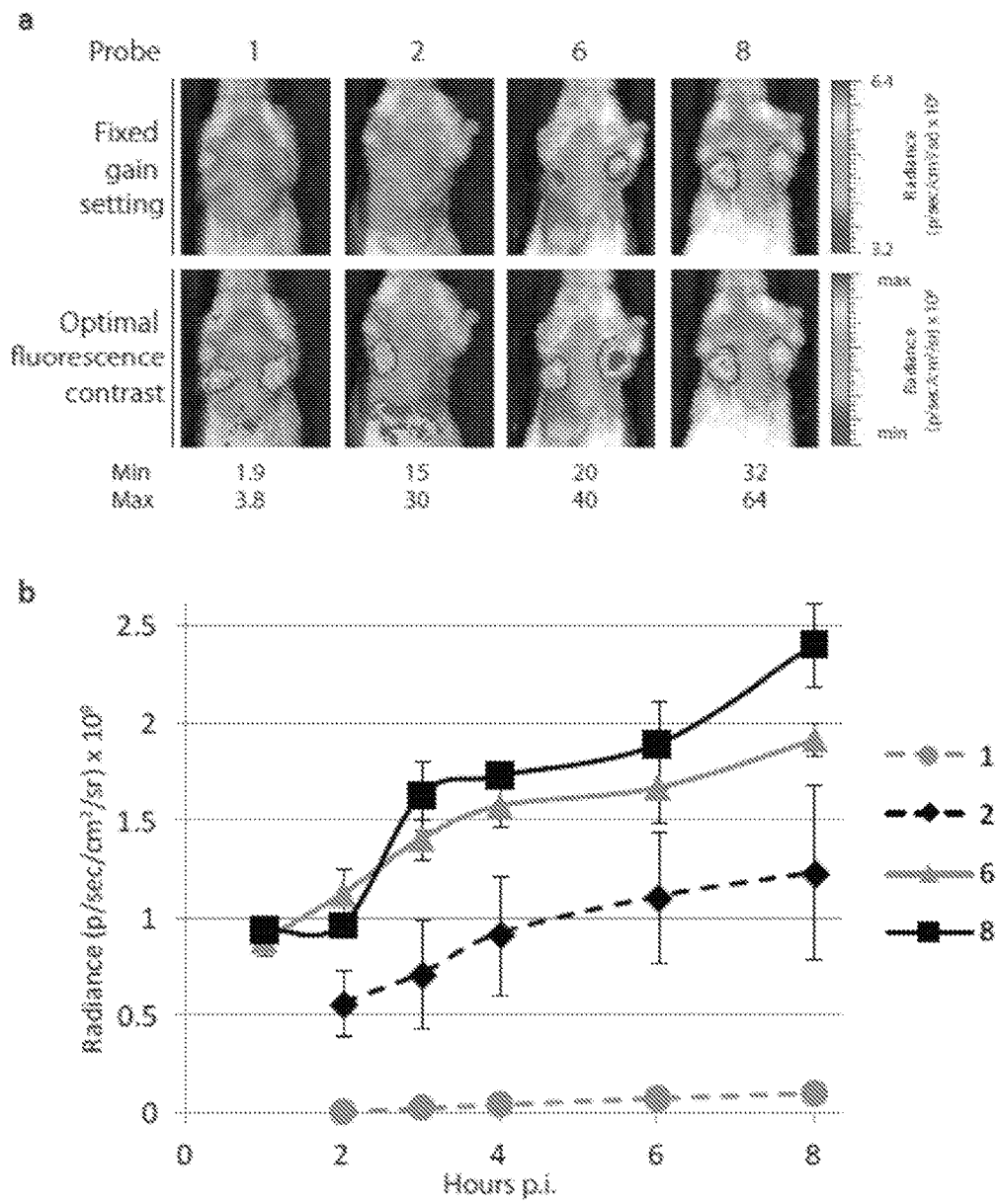
FIG. 5. a) Non-invasive optical imaging of tumor bearing mice 8 hours post injection of probe 1, 2, 6 or 8. The lower panels represent the optimal fluorescence contrast at each time point. b) Time-dependent tumor-specific fluorescence (tumor—background) for mice treated with probe 1, 2, 6 or 8 (n=3; data represent mean values±standard errors). c) Ex vivo tumor fluorescence (top panel) and in vivo fluorescently labeled proteins after SDS-PAGE visualized by in-gel fluorescence scanning (lower panel). d) Fluorescence intensity of end point of noninvasive optical imaging (shown in a), ex vivo tumor imaging, and in-gel fluorescence labeling (shown in c). Intensity relative to probe 1 is depicted (n=3; data represent mean values±standard errors). e) Fluorescence microscopy of probe 8 (first, third, and fourth columns) treated tumor tissue section with CD68 immuno-staining (second, third, and fourth columns) and nuclear staining (DAPI—third and fourth columns, scale bar 50 µm). No probe control (middle row panels) and iso-type control for immuno-staining (lower row panels) are depicted). 0 Colocalization diagram for probe 8 (Cy5) and CD68 (FITC).
Figure 5:
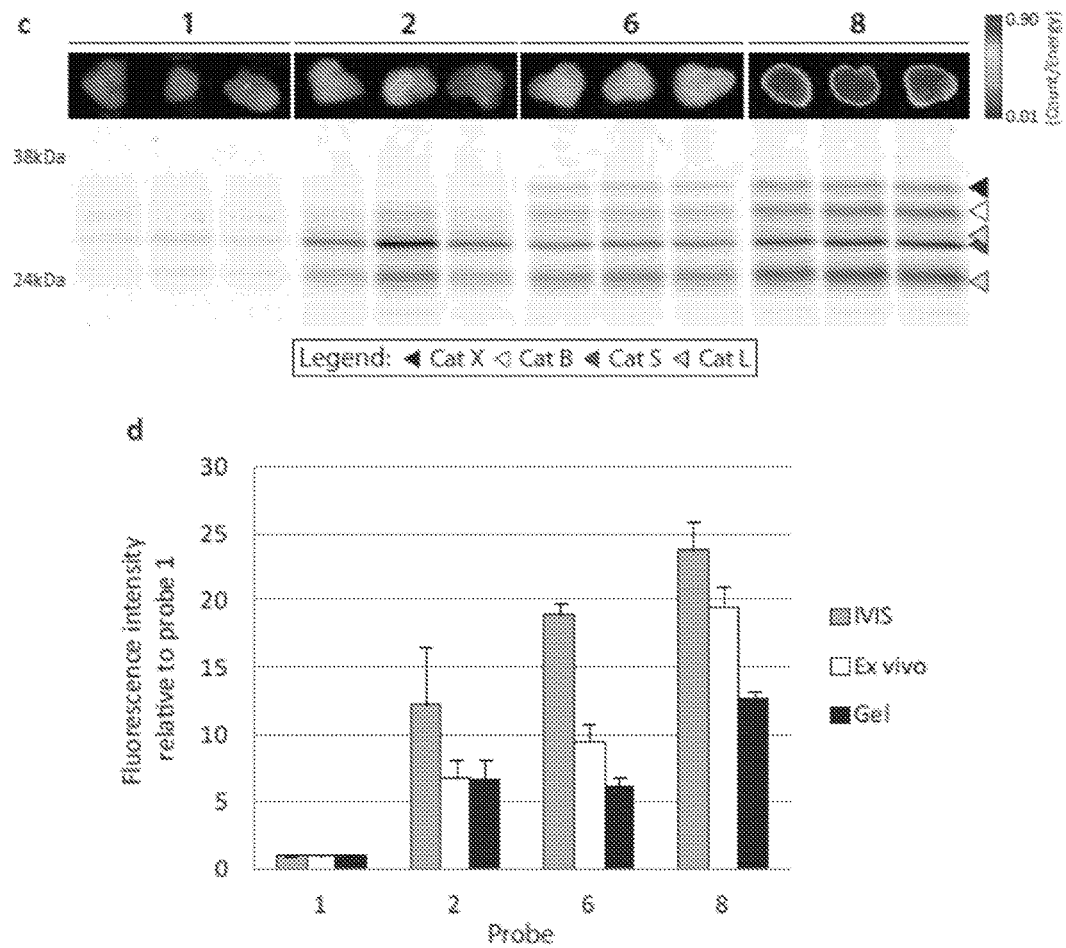
Figure 5:
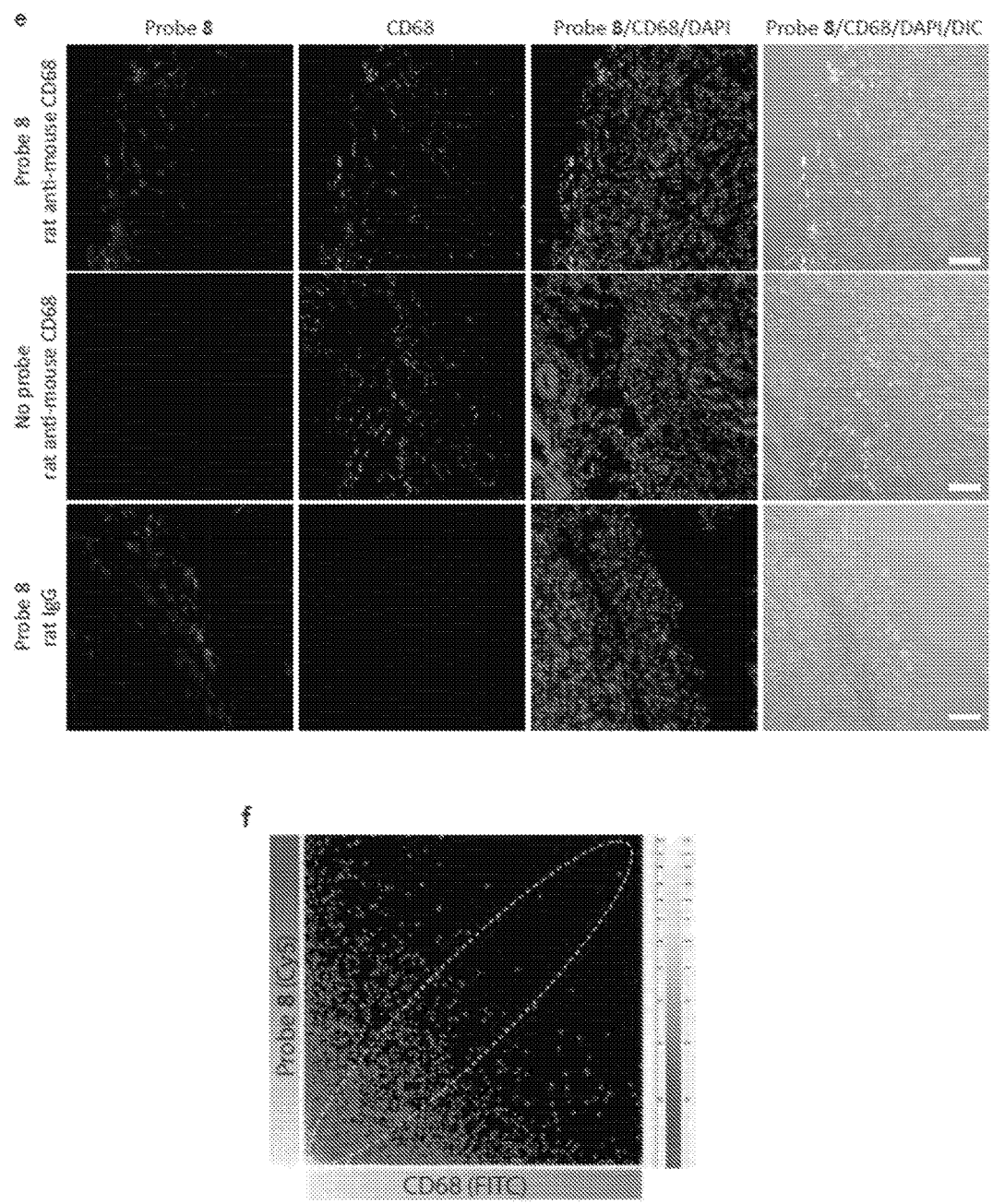

Given the positive live cell labeling propertied of the new PMK electrophile, the best performing PMK qABPs 2, 6 and 8 were tested in an orthotopic mouse model of breast cancer. Tao et al. (2008) *BMC Cancer* 8:228. In addition these PMK probes were compared to the original AOMK probe 1 (FIG. 3 and FIG. 5). 4T1 cells were implanted in the number 2 and 7 mammary fat pads of Balb/c mice, and tumor growth was monitored. When tumors were established, the mice were injected with equimolar amounts of qABPs (20 nmol) via tail vein, and the Cy5 fluorescence was noninvasively imaged over time (FIG. 3a,b). Again, these results confirmed that the qABP 8 proved to be superior. Robust tumor-specific activation of fluorescence could be observed for probe 8 specifically in the tumor region with high overall contrast. This signal continued to increase over time up to the end of the time course. Ultimately probe 8 achieved a more than twenty fold enhanced tumor specific fluorescence signal compared to probe 1. Good tumor specific contrast was also observed for probe 6 and to a lesser extent for probe 2, although both still outcompeted probe 1 by more than tenfold (FIG. 5a,b). After the completion of the time course, the tumors were excised and tumor fluorescence was measured ex vivo, followed by homogenization and analysis of the fluorescently labeled proteins by SDS-PAGE (FIG. 3c and FIG. 5c). The quantification of the ex vivo fluorescence and the total cysteine cathepsin labeling showed a similar trend as seen in the noninvasive optical imaging studies (FIG. 3d and FIG. 5d). To determine the cellular source of the probe fluorescence, immuno-fluorescence staining of tumor tissue sections from probe labeled mice were stained using the macrophage marker CD68 (FIG. 3e and FIG. 5e). Cy5 fluorescence localized to CD68 positive cells, however, not all CD68 positive cells were also probe 8 positive, indicating different activation states of the tumor-associated macrophages. More detailed analysis with confocal laser scanning microscopy (CLSM) confirmed that all cells that were positive for probe 8 were CD68 positive, but that probe labeled cathepsins and the CD68 signals do not co-localize to the same vesicles (FIG. 3f and FIG. 5f). Taken together, these data confirm that increasing the hydrophilicity of the quencher, shortening of the spacer and the introduction of a more reactive and sterically less restricted nucleophilic trap resulted in a qABP with a broad cysteine cathepsin reactivity and overall improved in vivo properties.

Although very distinct functions have been described for some of the cysteine cathepsin family members, (Conus & Simon (2010) *Swiss Med. Wkly.* 140:w13042) other roles are redundant and alterations in the activity of one cathepsin can influence the activity of others. For example, loss of cathepsin B is compensated by increased activity of cathepsin X (Sevenich et al. (2010) *Proc. Natl Acad. Sci. USA* 107:2497-502) and upregulation of cathepsin B results in downregulation of cathepsin L (Gopinathan et al. (2012) *Gut* 61:877-84). Therefore a broad spectrum probe is highly valuable as it facilitates the readout of multiple cysteine cathepsins in one experiment and enables the comparison of the activities of the individual cathepsins with respect to one another. The usefulness of such pan-reactive ABPs has been demonstrated by the pan-serine hydrolase fluorophosphonate probes (Liu et al. (1999) *Proc. Natl Acad. Sci. USA* 96:14694-9) and the pan-reactive proteasome probe MV151 (Verdoes et al. (2006) *Chem. Biol.* 13:1217-26). Furthermore, because the PMK-based qABPs are highly reactive towards cathepsin X these scaffolds can be used to generate selective qABPs against this still poorly understood cysteine cathepsin. (Paulick & Bogyo (2011) *ACS Chem. Biol.* 6:563-72).

In conclusion, a novel class of quenched fluorescent activity-based probes have been synthesized bearing a PMK electrophile with greater reactivity and broader selectivity compared to the previously reported AOMK based probes. The hydrophilicity of the qABP has furthermore been increased by introducing a sulfonated quencher and shortening the spacer tethering the electrophile and the quencher, resulting in greater aqueous solubility and improved in vivo properties resulting in enhanced contrast in noninvasive optical imaging of cancer.

Methods

General

All resins and reagents were purchased from commercial suppliers and used without further purifications. All solvents used were HPLC grade. All water-sensitive reactions were performed in anhydrous solvents under positive pressure of argon. Reactions were analyzed by LC-MS using an API 150EX single-quadrupole mass spectrometer (Applied Biosystems). Reverse-phase HPLC was conducted with an ÄKTA explorer 100 (Amersham Pharmacia Biotech) using C18 columns. NMR spectra were recorded on a Varian 400 MHz (400/100), Varian 500 MHz (500/125) or a Varian Inova 600 MHz (600/150 MHz) equipped with a pulsed field gradient accessory. Chemical shifts are given in ppm ($\delta$) relative to tetramethylsilane as an internal standard. Coupling constants are given in Hz. Fluorescent gels were scanned using a Typhoon 9400 flatbed laser scanner (GE Healthcare). In-gel labeling intensities were quantified using Image J software. Statistical analysis was performed using Microsoft Excel, and s.e.m. was calculated by dividing the s.d. by the square root of n. Fluorescent microscopy images were acquired on a Zeiss confocal LSM 710 and a Zeiss Axiovert 200 M inverted microscope equipped with a 10×, 40× and 63× objective (Carl Zeiss). Slidebook software was used to control the microscope and camera and for data analysis (Intelligent Imaging Innovations).

qABP Synthesis

The synthetic scheme for synthesis of the following compounds is depicted below in Scheme 1.

2,6-dimethyl-4-((6-(tritylamino)hexyl)carbamoyl)benzoic acid (11a). Mono-trityl 1,6-diaminohexane acetic acid salt (9a) (117.2 mg, 0.28 mmol) was taken up in DCM and washed with sat. aq. NaHCO$_3$, dried over Na$_2$SO$_4$ and concentrated in vacuo. The amine was dissolved in DMF and HOBt monohydrate (43 mg, 0.28 mmol, 1 equiv.), EDC (54 mg, 0.28 mmol, 1 equiv.) and 2,6-dimethylterephthalic acid (10) (54.4 mg, 0.28 mmol, 1 equiv.) were added and the reaction mixture was stirred overnight, before being concentrated in vacuo. The crude was purified by flash column chromatography (DCM→5% MeOH in DCM) and subsequently taken up in DCM and washed with water and dried over MgSO$_4$ to yield 70 mg (0.13 mmol, 47% isolated yield).

2,6-dimethyl-4-((2-(tritylamino)ethyl)carbamoyl)benzoic acid (11b). Mono-trityl ethylenediamine acetic acid salt (9b) (97.9 mg, 0.27 mmol) was taken up in DCM and washed with sat. aq. NaHCO$_3$, dried over Na$_2$SO$_4$ and concentrated in vacuo. The amine was dissolved in DMF and HOBt monohydrate (43 mg, 0.28 mmol, 1.04 equiv.), EDC (61 mg, 0.32 mmol, 1.2 equiv.) and 2,6-dimethylterephthalic acid (10) (52 mg, 0.27 mmol, 1 equiv.) were added and the reaction mixture was stirred overnight, before being concentrated in vacuo. The crude was purified by flash column chromatography (DCM→5% MeOH in DCM) and subsequently taken up in DCM and washed with water and dried over MgSO$_4$ to yield 28 mg (0.06 mmol, 22% isolated yield).

2,3,5,6-tetrafluoro-4-hydroxy-N-(6-(tritylamino)hexyl) benzamide (13a). Mono-trityl 1,6-diaminohexane acetic acid salt (9a) (117.2 mg, 0.28 mmol) was taken up in DCM and washed with sat. aq. NaHCO$_3$, dried over Na$_2$SO$_4$ and concentrated in vacuo. The amine was dissolved in DMF and HOBt monohydrate (43 mg, 0.28 mmol, 1 equiv.), EDC (54 mg, 0.28 mmol, 1 equiv.) and 2,3,5,6-tetrafluoro-4- hydroxybenzoic acid (12) (59 mg, 0.28 mmol, 1 equiv.) were added and the reaction mixture was stirred overnight, before being concentrated in vacuo. The crude was purified by flash column chromatography (15%→30% ethyl acetate in hexane) to yield 90 mg (0.16 mmol, 58% isolated yield).

2,3,5,6-tetrafluoro-4-hydroxy-N-(2-(tritylamino)ethyl) benzamide (13b). Mono-trityl ethylenediamine acetic acid salt (9b) (100 mg, 0.28 mmol) was taken up in DCM and washed with sat. aq. NaHCO$_3$, dried over Na$_2$SO$_4$ and concentrated in vacuo. The amine was dissolved in DMF and HOBt monohydrate (43 mg, 0.28 mmol, 1 equiv.), EDC (54 mg, 0.28 mmol, 1 equiv.) and 2,3,5,6-tetrafluoro-4-hydroxybenzoic acid (12) (59 mg, 0.28 mmol, 1 equiv.) were added and the reaction mixture was stirred overnight, before being concentrated in vacuo. The crude was purified by flash column chromatography (20%→35% ethyl acetate in hexane) to yield 90 mg (0.18 mmol, 65% isolated yield). $^1$H NMR (400 MHz, DMSO) δ=8.77 (t, J=6.0, 1H), 7.39 (d, J=7.8, 6H), 7.27 (t, J=7.7, 6H), 7.17 (t, J=7.2, 3H), 3.40-3.35 (m, 2H), 2.86-2.77 (m, 1H), 2.14-2.04 (m, 2H).

Scheme 1.

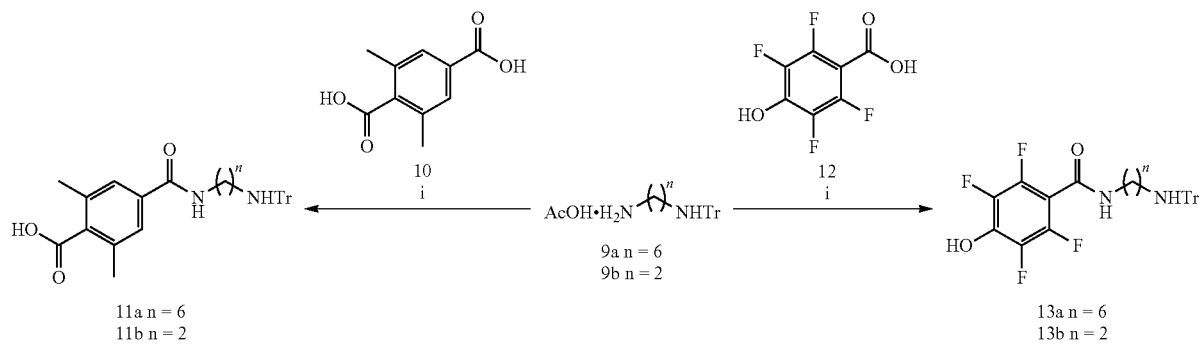

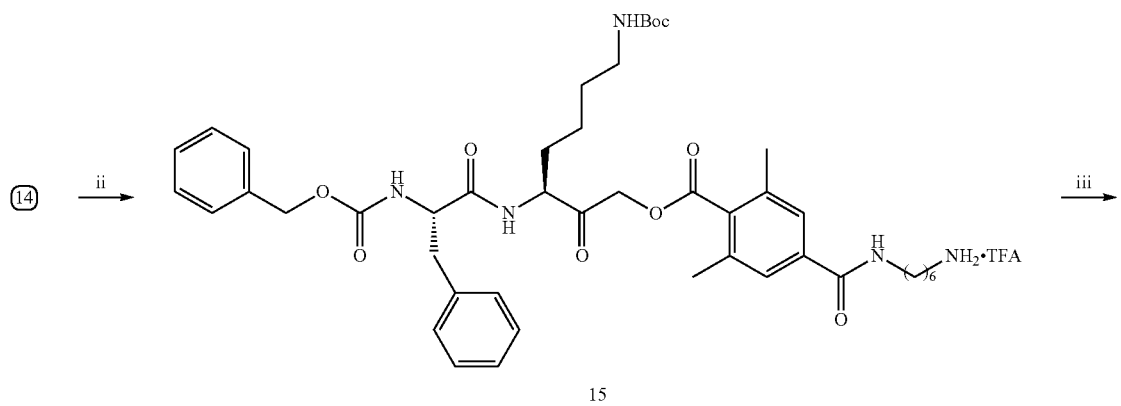

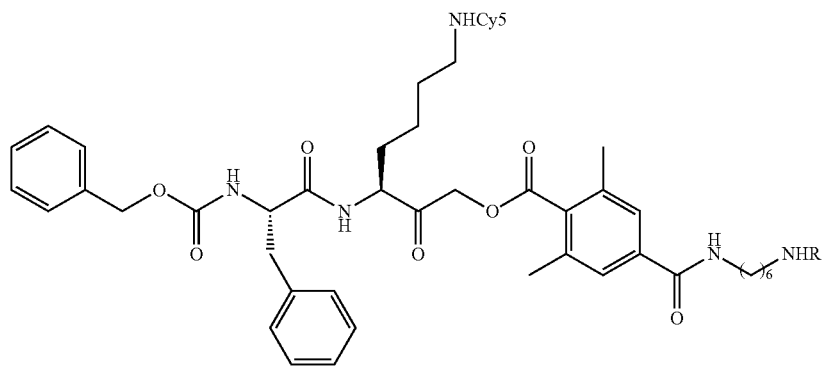

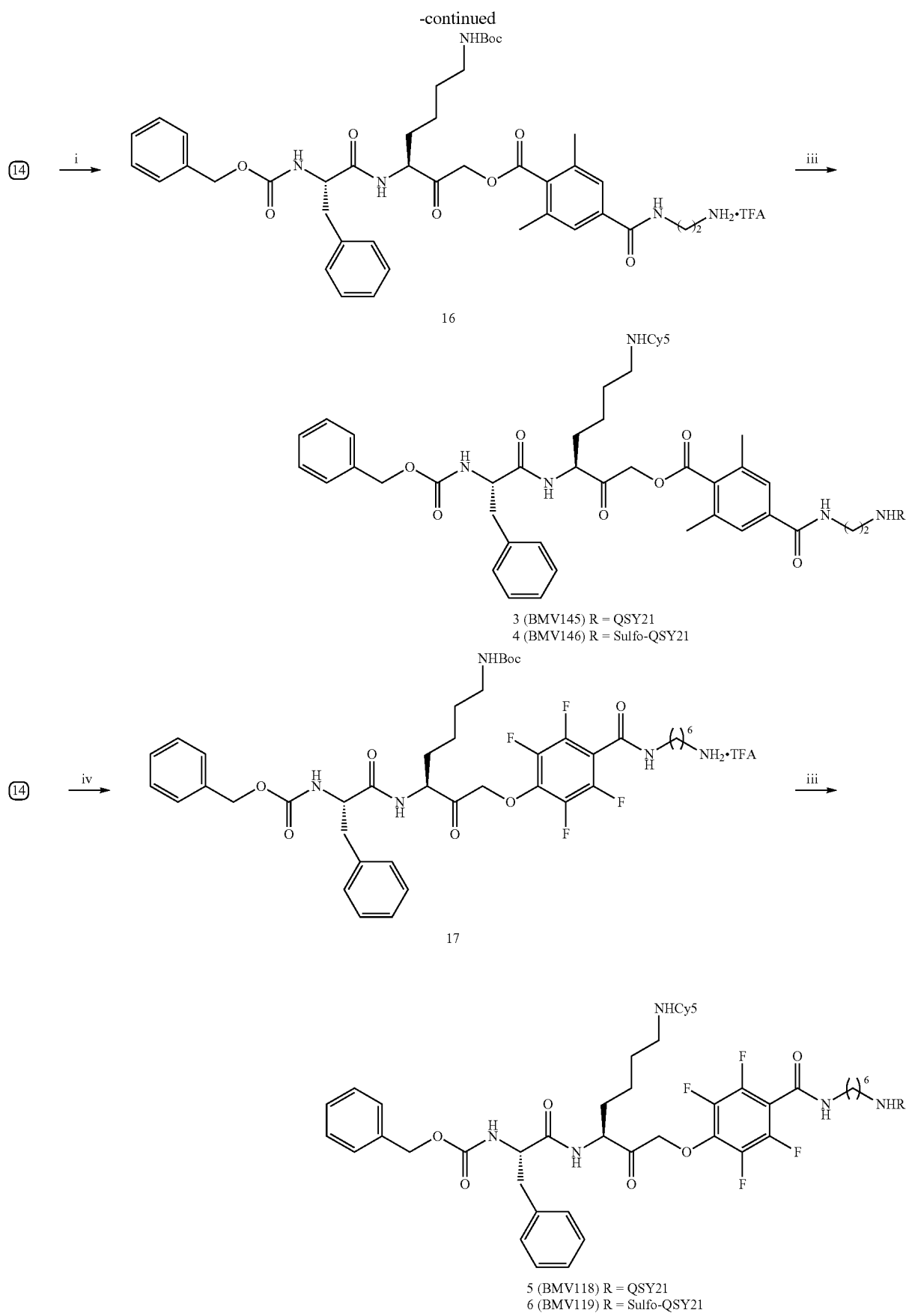

-continued
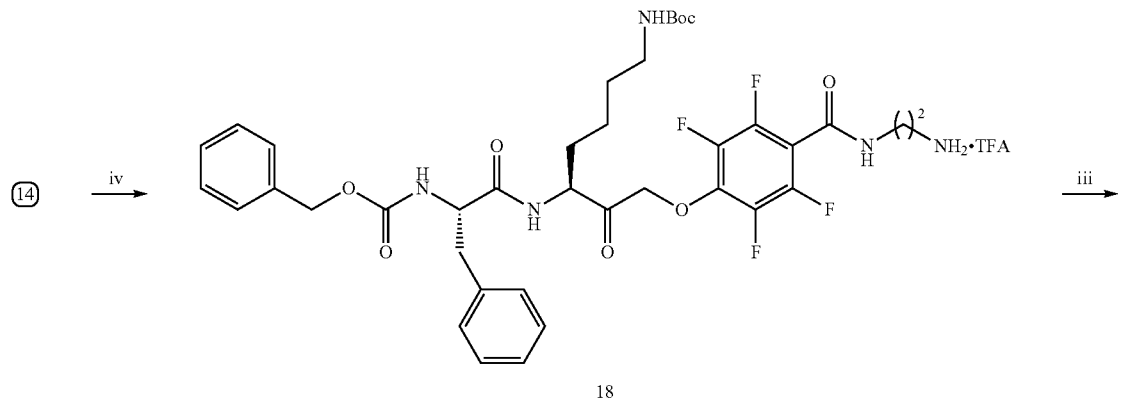
18
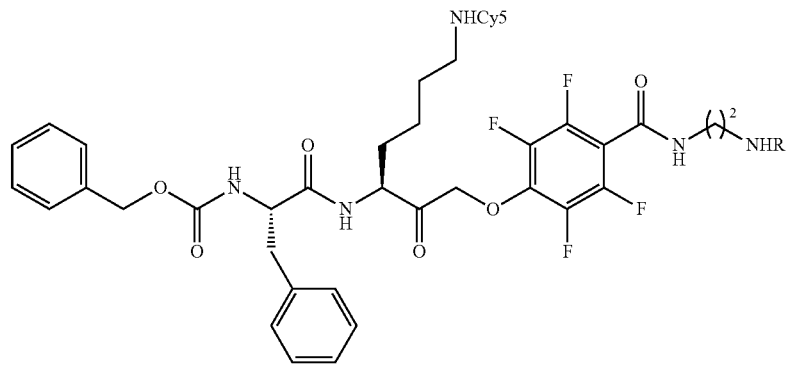
7 (BMV108) R = QSY21
8 (BMV109) R = Sulfo-QSY21
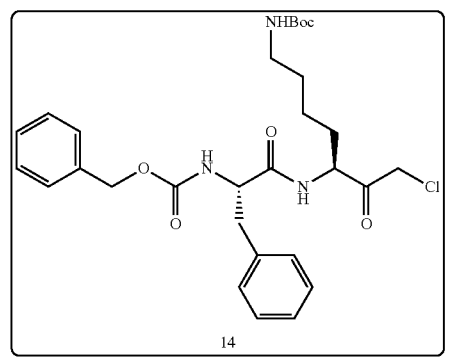
14

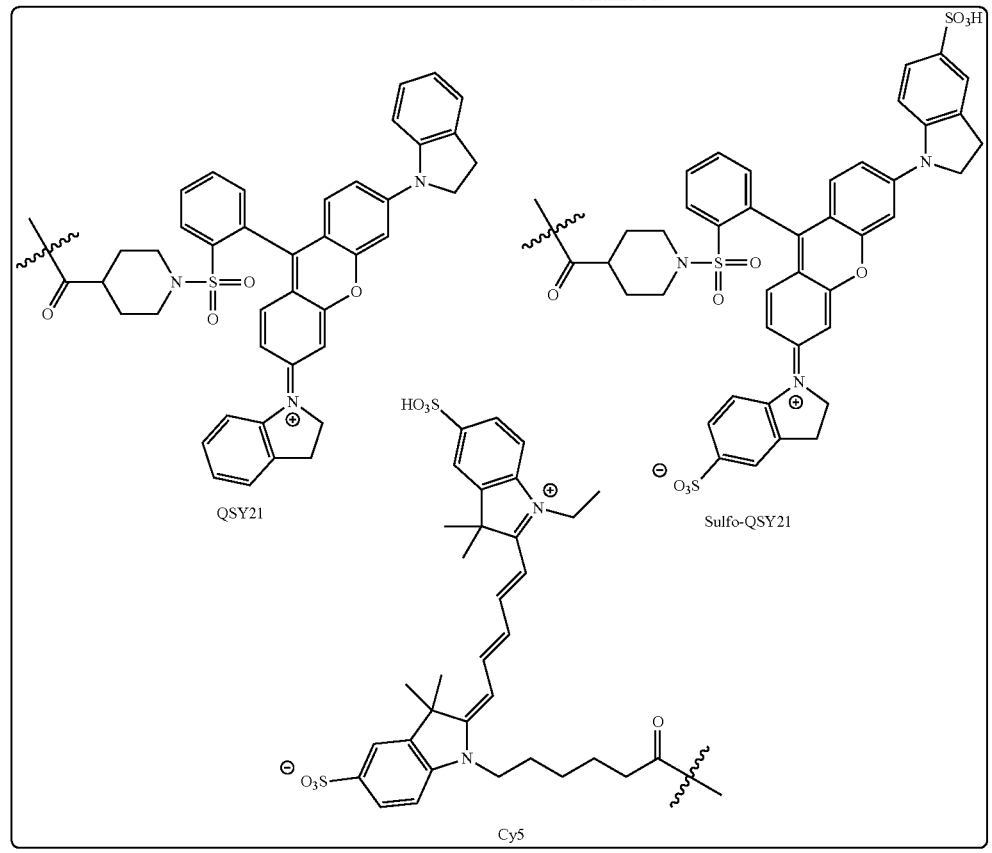

Reagents and conditions: i. EDC, HOBt, DMF. ii. a) KF, DMF. b) 1% TFA, DCM. iii. a) QSY21-NHS or Sulfo-QSY21-NHS, DiPEA, DMSO. b) TFA/DCM = 1/1. c) Cy5-NHS, DiPEA, DMSO. iv. a) KF, DMF, 80° C. b) 1% TFA, DCM.

Intermediate 15. Potassium fluoride (3 mg, 52 µmol, 3 equiv.) was suspended in DMF by sonication for 5 min, after which carboxylic acid 11a (10 mg, 19 µmol, 1.1 equiv.) was added. The reaction mixture was stirred for 10 min, before chloromethyl ketone 14 (9.7 mg, 17.3 µmol, 1 equiv.) was added. After 2 hr the reaction mixture was concentrated in vacuo and the crude was taken up in 1% TFA in DCM and stirred for 30 min, before being quenched by the addition of triisopropylsilane until the solution was colorless. After coevaporation with toluene (3×) the title compound was purified by HPLC (preparatory reverse phase $C_{18}$ column, $CH_3CN/H_2O$ 0.1% TFA, 15:85 to 55:45 over 20 min; 5 mL/min), followed by lyophilization to afford 15 as a white powder (3.12 mg, 3.46 µmol, 20% over 2 steps).

Intermediate 16. Potassium fluoride (3 mg, 52 µmol, 3 equiv.) was suspended in DMF by sonication for 5 min, after which carboxylic acid 11b (9.5 mg, 20 µmol, 1.1 equiv.) was added. The reaction mixture was stirred for 10 min, before chloromethyl ketone 14 (10 mg, 17.9 µmol, 1 equiv.) was added. After 1.5 hr the reaction mixture was concentrated in vacuo and the crude was taken up in 1% TFA in DCM and stirred for 30 min, before being quenched by the addition of triisopropylsilane until the solution turned colorless. After coevaporation with toluene (3×) intermediate 16 was purified by HPLC (preparatory reverse phase $C_{18}$ column, $CH_3CN/H_2O$ 0.1% TFA, 15:85 to 55:45 over 20 min; 5 mL/min), followed by lyophilization to afford a white powder (3.99 mg, 4.57 µmol, 26% over 2 steps). $^1$H NMR (500 MHz, $CD_3OD$) δ 7.80 (s, 1H), 7.42 (s, 1H), 7.35-7.18 (m, 10H), 5.06 (s, 2H), 4.85-4.78 (m, 2H), 4.42 (dd, J=13.1, 6.2 Hz, 1H), 4.37 (dd, J=10.1, 4.0 Hz, 1H), 3.64 (t, J=5.7 Hz, 2H), 3.18 (t, J=4.8 Hz, 2H), 3.12 (dd, J=13.7, 7.0 Hz, 1H), 3.01 (t, J=7.3 Hz, 2H), 2.94 (dd, J=13.6, 8.9 Hz, 1H), 2.41 (s, 3H), 2.34 (s, 3H), 1.92-1.82 (m, 1H), 1.67-1.57 (m, 1H), 1.49-1.26 (m, 4H), 1.42 (s, 9H).

Intermediate 17. Potassium fluoride (6.3 mg, 108 µmol, 3 equiv.) was suspended in DMF by sonication for 5 min, after which phenol 13a (21.5 mg, 39 µmol, 1.1 equiv.) was added. The reaction mixture was stirred for 10 min, before chloromethyl ketone 14 (20 mg, 36 µmol, 1 equiv.) was added. The reaction mixture was stirred at 80° C. for 5 hr, before being concentrated in vacuo. The crude was taken up in 1% TFA in DCM and stirred for 30 min, before being quenched by the addition of triisopropylsilane until the solution turned colorless. After coevaporation with toluene (3×), purification by HPLC (preparatory reverse phase $C_{18}$ column, $CH_3CN/H_2O$ 0.1% TFA, 25:75 to 70:30 over 20 min; 5 mL/min), followed by lyophilization afforded the title compound as a white powder (16.6 mg, 17.5 µmol, 49% over 2 steps). $^1$H NMR (500 MHz, $CD_3OD$) δ 7.29 (m, 10H), 5.07 (s, 2H), 4.86 (m, 2H), 4.44 (m, 2H), 3.41 (t, J=6.8, 2H), 3.10 (dd, J=13.5, 7.0, 1H), 3.02 (t, J=6.8, 2H), 2.97-2.91 (m, 3H), 1.93-1.81 (m, 1H), 1.73-1.62 (m, 4H), 1.62-1.53 (m, 1H), 1.51-1.46 (m, 4H), 1.43 (s, 9H), 1.45-1.25 (m, 4H).

Intermediate 18. Potassium fluoride (6.3 mg, 108 µmol, 3 equiv.) was suspended in DMF by sonication for 5 min, after which phenol 13b (19.4 mg, 39 µmol, 1.1 equiv.) was added. The reaction mixture was stirred for 10 min, before chloromethyl ketone 14 (20 mg, 36 µmol, 1 equiv.) was added. The reaction mixture was stirred at 80° C. for 3 hr, before being concentrated in vacuo. The crude was taken up in 1% TFA in DCM and stirred for 30 min, before being quenched by the addition of triisopropylsilane until the solution turned colorless. After coevaporation with toluene (3×), purification by HPLC (preparatory reverse phase $C_{18}$ column, $CH_3CN/H_2O$ 0.1% TFA, 20:80 to 60:40 over 20 min; 5 mL/min), followed by lyophilization afforded the title compound as a white powder (15.4 mg, 17.3 µmol, 48% over 2 steps). $^1$H NMR (400 MHz, $CD_3OD$) δ=7.36-7.12 (m, 10H), 5.05 (s, 2H), 4.86-4.81 (m, 2H), 4.42-4.37 (m, 2H), 3.64 (t, J=6.5, 2H), 3.14 (t, J=6.5, 2H), 3.08 (dd, J=13.9, 7.2, 1H), 2.99 (t, J=6.5, 2H), 2.91 (dd, J=13.9, 8.4, 1H), 1.90-1.78 (m, 1H), 1.62-1.48 (m, 1H), 1.41 (s, 9H), 1.46-1.20 (m, 4H).

Probe 1 (GB137). Intermediate 15 (1.5 mg, 1.7 µl) was taken up in DMSO (50 µl) and QSY21-NHS (1.39 mg, 1.7 µmol, 1 equiv.) and DiPEA (1.5 µl, 8.5 µmol, 5 equiv.) were added. After 1 hr the QSY21 amide was purified by HPLC (preparatory reverse phase $C_{18}$ column, $CH_3CN/H_2O$ 0.1% TFA, 40:60 to 80:20 over 20 min; 5 mL/min), followed by lyophilization. To remove the Boc protective group the resulting dark blue powder was taken up in TFA/DCM (1/1) and reacted for 30 min, before coevaporation with toluene (3×) to give 2.42 mg of the corresponding TFA salt (1.6 µmol, 95% over 2 steps). The amine was dissolved in DMSO (50 µl) and Cy5-NHS (1.3 mg, 1.76 µmol, 1.1 equiv.) and DiPEA (1.4 µl, 8 µmol, 5 equiv.) were added. After 1 hr, purification by HPLC (preparatory reverse phase $C_{18}$ column, $CH_3CN/H_2O$ 0.1% TFA, 40:60 to 75:25 over 20 min; 5 mL/min), followed by lyophilization afforded probe 1 as a dark blue powder (2.0 mg, 0.99 µmol, 62%).

Probe 2 (BMV122). Intermediate 15 (1.5 mg, 1.7 µl) was taken up in DMSO (50 µl) and Sulfo-QSY21-NHS (1.66 mg, 1.7 µmol, 1 equiv.) and DiPEA (1.5 µl, 8.5 µmol, 5 equiv.) were added. After 1 hr the Sulfo-QSY21 amide was purified by HPLC (preparatory reverse phase $C_{18}$ column, $CH_3CN/H_2O$ 0.1% TFA, 30:70 to 70:30 over 20 min; 5 mL/min), followed by lyophilization. To remove the Boc protective group the resulting dark blue powder was taken up in TFA/DCM (1/1) and reacted for 30 min, before coevaporation with toluene (3×) to give 2.29 mg of the corresponding TFA salt (1.39 µmol, 81% over 2 steps). The amine was dissolved in DMSO (50 µl) and Cy5-NHS (1.1 mg, 1.5 µmol, 1.1 equiv.) and DiPEA (1.2 µl, 7 µmol, 5 equiv.) were added. After 1 hr, purification by HPLC (preparatory reverse phase $C_{18}$ column, $CH_3CN/H_2O$ 0.1% TFA, 15:85 to 50:50 over 20 min; 5 mL/min), followed by lyophilization afforded probe 2 as a dark blue powder (1.83 mg, 0.84 µmol, 61%).

Probe 3 (BMV145) Intermediate 16 (1.5 mg, 1.7 µl) was taken up in DMSO (50 µl) and QSY21-NHS (1.39 mg, 1.7 µmol, 1 equiv.) and DiPEA (1.5 µl, 8.5 µmol, 5 equiv.) were added. After 1 hr the QSY21 amide was purified by HPLC (preparatory reverse phase $C_{18}$ column, $CH_3CN/H_2O$ 0.1% TFA, 40:60 to 80:20 over 20 min; 5 mL/min), followed by lyophilization. To remove the Boc protective group the resulting dark blue powder was taken up in TFA/DCM (1/1) and reacted for 30 min, before coevaporation with toluene (3×) to give 0.86 mg of the corresponding TFA salt (0.6 µmol, 35% isolated yield over 2 steps). The amine was dissolved in DMSO (50 µl) and Cy5-NHS (0.5 mg, 0.66 µmol, 1.1 equiv.) and DiPEA (0.57 µl, 3.3 µmol, 5 equiv.) were added. After 1 hr, purification by HPLC (preparatory reverse phase $C_{18}$ column, $CH_3CN/H_2O$ 0.1% TFA, 40:60 to 75:25 over 20 min; 5 mL/min), followed by lyophilization afforded probe 3 as a dark blue powder (0.67 mg, 0.34 µmol, 57%).

Probe 4 (BMV146). Intermediate 16 (1.0 mg, 1.2 µl) was taken up in DMSO (50 µl) and Sulfo-QSY21-NHS (1.25 mg, 1.2 µmol, 1 equiv.) and DiPEA (1.05 µl, 6 µmol, 5 equiv.) were added. After 1 hr the Sulfo-QSY21 amide was purified by HPLC (preparatory reverse phase $C_{18}$ column, $CH_3CN/H_2O$ 0.1% TFA, 20:80 to 80:20 over 20 min; 5 mL/min), followed by lyophilization. To remove the Boc protective group the resulting dark blue powder was taken up in TFA/DCM (1/1) and reacted for 30 min, before coevaporation with toluene (3×) to give 1.06 mg of the corresponding TFA salt (0.66 µmol, 55% over 2 steps). The amine was dissolved in DMSO (50 µl) and Cy5-NHS (0.55 mg, 0.73 µmol, 1.1 equiv.) and DiPEA (0.64 µl, 3.65 µmol, 5 equiv.) were added. After 1 hr, purification by HPLC (preparatory reverse phase $C_{18}$ column, $CH_3CN/H_2O$ 0.1% TFA, 15:85 to 50:50 over 20 min; 5 mL/min), followed by lyophilization afforded probe 4 as a dark blue powder (0.63 mg, 0.3 µmol, 45%).

Probe 5 (BMV118). Intermediate 17 (1.2 mg, 1.3 µl) was taken up in DMSO (50 µl) and QSY21-NHS (1.0 mg, 1.3 µmol, 1 equiv.) and DiPEA (1.13 µl, 6.5 µmol, 5 equiv.) were added. After 2 hr the QSY21 amide was purified by HPLC (preparatory reverse phase $C_{18}$ column, $CH_3CN/H_2O$ 0.1% TFA, 40:60 to 80:20 over 20 min; 5 mL/min), followed by lyophilization. To remove the Boc protective group the resulting dark blue powder was taken up in TFA/DCM (1/1) and reacted for 30 min, before coevaporation with toluene (3×) to give 2.0 mg of the corresponding TFA salt (1.3 µmol, quantitative over 2 steps). The amine was dissolved in DMSO (50 µl) and Cy5-NHS (1.0 mg, 1.3 µmol, 1 equiv.) and DiPEA (1.1 µl, 6.5 µmol, 5 equiv.) were added. After 1 hr, purification by HPLC (preparatory reverse phase $C_{18}$ column, $CH_3CN/H_2O$ 0.1% TFA, 40:60 to 85:15 over 20 min; 5 mL/min), followed by lyophilization afforded probe 5 as a dark blue powder (1.91 mg, 0.94 µmol, 72%).

Probe 6 (BMV119). Intermediate 17 (1.2 mg, 1.3 µl) was taken up in DMSO (50 µl) and Sulfo-QSY21-NHS (1.35 mg, 1.3 µmol, 1 equiv.) and DiPEA (1.13 µl, 6.5 µmol, 5 equiv.) were added. After 1 hr the Sulfo-QSY21 amide was purified by HPLC (preparatory reverse phase $C_{18}$ column, $CH_3CN/H_2O$ 0.1% TFA, 30:70 to 90:10 over 20 min; 5 mL/min), followed by lyophilization. To remove the Boc protective group the resulting dark blue powder was taken up in TFA/DCM (1/1) and reacted for 30 min, before coevaporation with toluene (3×) to give 1.98 mg of the corresponding TFA salt (0.9 µmol, 70% over 2 steps). The amine was dissolved in DMSO (50 µl) and Cy5-NHS (0.7 mg, 0.9 µmol, 1.1 equiv.) and DiPEA (0.8 µl, 4.5 µmol, 5 equiv.) were added. After 1 hr, purification by HPLC (preparatory reverse phase $C_{18}$ column, $CH_3CN/H_2O$ 0.1% TFA, 15:85 to 50:50 over 20 min; 5 mL/min), followed by lyophilization afforded probe 6 as a dark blue powder (1.63 mg, 0.74 µmol, 82%).

Probe 7 (BMV108). Intermediate 18 (1.2 mg, 1.3 µl) was taken up in DMSO (50 µl) and QSY21-NHS (1.2 mg, 1.4 µmol, 1.1 equiv.) and DiPEA (1.13 µl, 6.5 µmol, 5 equiv.) were added. After 1 hr the QSY21 amide was purified by HPLC (preparatory reverse phase $C_{18}$ column, $CH_3CN/H_2O$ 0.1% TFA, 30:70 to 70:30 over 20 min; 5 mL/min), followed by lyophilization to afford a dark blue powder (1.43 mg, 0.99 µmol, 76%). The Boc protective group was subsequently removed in TFA/DCM (1/1) for 30 min, before coevaporation with toluene (3×). The TFA salt was dissolved in DMSO (50 µl) and Cy5-NHS (0.83 mg, 1.1 µmol, 1.1 equiv.) and DiPEA (0.88 µl, 5 µmol, 5 equiv.) were added. After 1 hr, purification by HPLC (preparatory reverse phase $C_{18}$ column, $CH_3CN/H_2O$ 0.1% TFA, 30:70 to 70:30 over 20 min; 5 mL/min), followed by lyophilization afforded probe 7 as a dark blue powder (0.95 mg, 0.48 µmol, 49% over 2 steps).

Probe 8 (BMV109). Intermediate 18 (5.8 mg, 6.5 µl) was dissolved in DMSO (100 µl). Sulfo-QSY21-NHS (9.75 mg, 10.39 µmol, 1.6 equiv.) and DiPEA (8.4 µl, 50.5 µmol, 7.8 equiv.) were added and the mixture was stirred overnight. The Sulfo-QSY21 amide was purified by HPLC (preparatory reverse phase $C_{18}$ column, $CH_3CN/H_2O$ 0.1% TFA, 25:75 to 55:45 over 20 min; 5 mL/min), followed by lyophilization to afford a dark blue powder. The Boc protective group was subsequently removed in TFA/DCM (1/1) for 30 min, before coevaporation with toluene (3×). The residue was dissolved in DMSO (250 µl) and Cy5-NHS (10.5 mg, 13.9 µmol, 2.1 equiv.) and DiPEA (12 µl, 72 µmol, 11 equiv.) were added. After 4 hr, purification by HPLC (preparatory reverse phase $C_{18}$ column, $CH_3CN/H_2O$ 0.1% TFA, 25:75 to 45:55 over 20 min; 5 mL/min), followed by lyophilization afforded probe 8 as a dark blue powder (7.74 mg, 4.61 µmol, 71% over 3 steps). $^1$H NMR (600 MHz, $CD_3CN$) δ 8.12-8.08 (m, 1H), 8.01-7.93 (m, 2H), 7.89-7.85 (m, 2H), 7.75 (dd, J=12.0, 1.5 Hz, 2H), 7.72 (dd, J=8.4, 1.7 Hz, 1H), 7.69 (dd, J=8.3, 1.2 Hz, 1H), 7.66 (s, 2H), 7.62-7.57 (m, 2H), 7.51 (dd, J=8.4, 5.1 Hz, 2H), 7.46 (d, J=9.4 Hz, 2H), 7.41-7.35 (m, 3H), 7.24 (s, 1H), 7.22 (s, 1H), 7.21-7.14 (m, 6H), 7.13-7.09 (m, 6H), 7.05 (dd, J=8.8, 4.6 Hz, 1H), 6.39 (t, J=12.8 Hz, 1H), 6.11 (t, J=12.6 Hz, 1H), 4.87 (q, J=12.7 Hz, 2H), 4.83 (dd, J=39.7, 14.1 Hz, 2H), 4.23-4.12 (m, 4H), 3.93 (q, J=7.2 Hz, 2H), 3.86 (t, J=7.4 Hz, 2H), 3.34 (dd, J=6.7, 4.1 Hz, 2H), 3.28-3.15 (m, 9H), 3.04-2.92 (m, 3H), 2.80-2.74 (m, 1H), 2.45 (t, J=11.9 Hz, 2H), 2.15-2.09 (m, 1H), 2.09-2.03 (m, 2H), 1.74-1.58 (m, 7H), 1.57 (s, 6H), 1.55 (s, 6H), 1.49 (dd, J=15.1, 7.4 Hz, 4H), 1.35-1.22 (m, 7H), 1.20 (t, J=7.3 Hz, 3H), 1.16-1.12 (m, 4H).

Cell Culture and Labeling of Living Cells and Cell Lysates

RAW cells were cultured in DMEM (GIBCO) supplemented with 10% fetal bovine serum (FBS; GIBCO), 100 units/mL penicillin and 100 µg/mL streptomycin (GIBCO). 4T1 cells (ATCC) were cultured in RPMI (GIBCO) supplemented with 10% fetal bovine serum (FBS; GIBCO), 100 units/mL penicillin and 100 µg/mL streptomycin (GIBCO). All cells were cultured in a 5% $CO_2$ humidified incubator at 37° C. For intact cell labeling, cells were exposed to probe (500× in DMSO) in culture media and incubated for 2 hr at 37° C., unless stated otherwise. Where indicated the cells were preincubated for 1 hr with the inhibitor JPM-OEt (500× in DMSO) or exposed to mouse serum (1 µl probe stock solution in DMSO added to 9 µl serum) for 4 hr before addition to the cells. After labeling, the cells were washed with PBS and resuspended in hypotonic lysis buffer (50 mM PIPES pH 7.4, 10 mM KCl, 5 mM $MgCl_2$, 2 mM EDTA, 4 mM DTT, and 1% NP-40) and put on ice for 15 min, centrifuged at 4° C. for 30 min and supernatants were collected, and protein concentration was determined using a BCA kit (pierce). 40 µg total protein was denatured be addition of 4× SDS-sample buffer and heating for 3 min at 100° C., resolved by SDS-PAGE (15%) and labeled proteases were visualized by scanning the gel with a Typhoon imager (GE Healthcare). Labeling intensities were quantified using Image J software. For cathepsin labeling in cell lysates, cells were harvested, washed with PBS and resuspended in citrate buffer (50 mM Citrate buffer pH 5.5, 5 mM DDT, 0.5% CHAPS, 0.1% Triton X). After 15 min on ice and centrifugation at 4° C. for 30 min the supernatants were collected, and protein concentration was determined using a BCA kit (pierce). 40 µg total protein was exposed to the indicated probe (200× in DMSO) for 1 hr at 37° C. 4× SDS-sample buffer was added and the protein was denatured for 3 min at 100° C. and analyzed as described above. For live cell microscopy RAW cells were seeded in phenol red-free complete medium at a density of $1 \cdot 10^5$ cells in 35 mm glass bottom dish (in vitro scientific) and were cultured overnight. The cells were either exposed to DMSO or 1 µM probe (500× in DMSO) for 2 hours. For the last hr, Lysotracker-green (200 nM final concentration, 1000× in DMSO) was added to the cells. Where indicated the cells were preincubated for 1 hr with the inhibitor JPM-OEt (500× in DMSO). Cells were imaged at 40× using a Zeiss Axiovert 200 M confocal microscope in both Cy5 and FITC channels.

Animal Models

All animal care and experimentation was conducted in accord with current National Institutes of Health and Stanford University Institutional Animal Care and Use Committee guidelines. Female BALB/c mice (6-8 weeks, The Jackson Laboratory) were injected in fat pad number 2 and 7 with $1 \cdot 10^5$ 4 T1 cells (ATCC) in PBS under isoflurane anesthesia and tumor growth was monitored. 24 hr before imaging the hair on the region of interest was removed using 'Nair lotion'. On day 10, the indicated probe (20 nmol; 0.8 nmol $g^{-1}$) was administered via tail vein in 100 µL volume (20% DMSO in PBS). After injection, mice were imaged noninvasively at indicated time points using an IVIS 100 system (Xenogen). The images were analyzed with Living Image software (PerkinElmer). After the last time point the mice were anesthetized with isofluorane and killed by cervical dislocation. For ex vivo fluorescence measurements and assessment of in vivo probe labeling profile tumors were removed, imaged using an FMT 2500 (PerkinElmer) and the tissue was sonicated (1 min on ice) in citrate buffer (50 mM Citrate buffer pH 5.5, 5 mM DDT, 0.5% CHAPS, 0.1% Triton X). After centrifugation at 4° C. for 30 min the supernatants were collected, and protein concentration was determined using a BCA kit (pierce). 40 µg total protein was denatured in SDS-sample buffer for 3 min at 100° C. and analyzed as described above. For immunofluorescence the resected tumors were incubated in a 4% PFA solution in PBS for 6 hr at 4° C. followed by overnight incubation in a 30% sucrose solution and freezing of the tissue in OCT medium. 6-µm sections were fixed in acetone, blocked with PNB blocking buffer and incubated with rat anti-mouse CD68 (1:1000; Serotec) overnight. Goat-anti Rat conjugated with AlexaFluor-488 (1:500; Invitrogen) was incubated for 1 hr at room temperature. Sections were then stained with DAPI (2 µg/mL; Invitrogen) for five minutes and then mounted in ProLong Gold Mounting Medium (Invitrogen). Tissues were then visualized using a Zeiss Axiovert 200M microscope.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A compound for use in labeling a protease having the structure of formula (I):

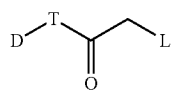

wherein

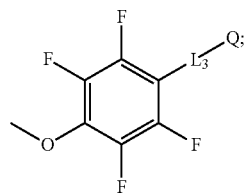

$L_3$ is an optionally substituted alkyl linker, wherein each carbon atom is optionally replaced with a heteroatom;
Q is a quencher;
T is a targeting element; and
D is a detectable element.

2. The compound of claim 1, wherein L is

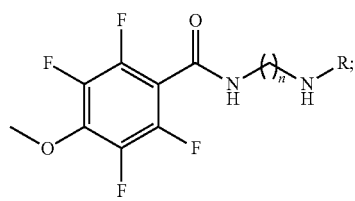

R is a QSY quencher; and
n is an integer from 1 to 16.

3. The compound of claim 2, wherein the QSY quencher is a hydrophilic QSY quencher.

4. The compound of claim 3, wherein the hydrophilic QSY quencher is a sulfo-QSY quencher.

5. A compound for use in labeling a protease having the structure of formula (II)

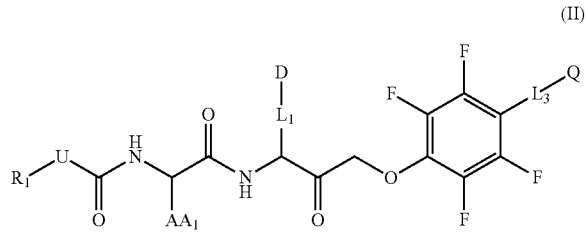

wherein $L_1$ is a linker;
$AA_1$ is an amino acid side chain;
U is O, N, or S;
$R_1$ is alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, or a protecting group, and is optionally substituted with 1 to 3 A groups;
each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamido, or azido;
D is a fluorescent label;
$L_3$ is a linker; and
Q is a quencher.

6. The compound of claim 5 having the structure of formula (III)

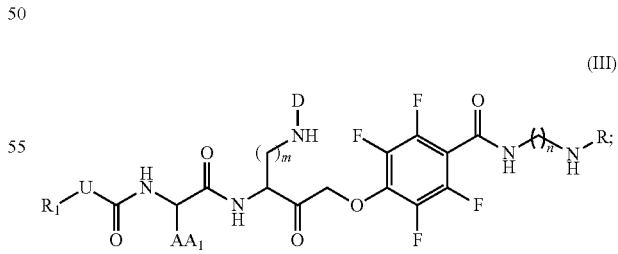

wherein R is a QSY quencher;
D is a cyanine dye; and
m and n are independently integers from 1 to 16.

7. The compound of claim 6, wherein R is QSY21 or sulfo-QSY21, and D is Cy5.

8. The compound of claim 7, selected from one of the following compounds:

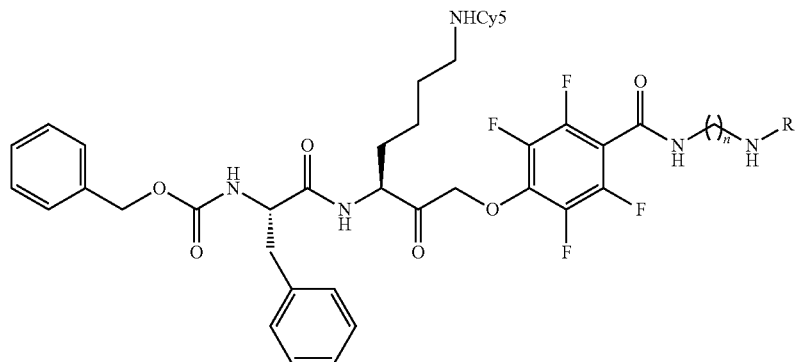

wherein R=QSY21 and n=6;
R=Sulfo-QSY21 and n=6;
R=QSY21 and n=2; and
R=Sulfo-QSY21 and n=2.

9. A composition for use in labeling a protease in an animal comprising the compound of claim 1 or 5 and a pharmaceutically acceptable carrier.

10. A method of labeling a protease in an animal comprising the step of:
administering the composition of claim 9 to the animal.

11. A method of visualizing a tumor in an animal comprising the steps of:
administering the composition of claim 9 to the animal; and
measuring a detectable signal generated in the animal from a reaction of the composition with a cathepsin cysteine protease; wherein the detectable signal is associated with a tumor in the animal.

12. The method of claim 11, wherein the detectable signal is a fluorescent signal.

13. The method of claim 12, wherein the fluorescent signal is generated at a tumor margin.

14. The compound of claim 1, wherein D is a fluorescent label, a radiolabel, or a chelator.

15. The compound of claim 14, wherein D is a fluorescent label.

16. The compound of claim 15, wherein the fluorescent label is a fluorescein, an Oregon green, a bora-diaza-indecene, a rhodamine, or a cyanine label.

17. The compound of claim 16, wherein the fluorescent label is a cyanine label.

18. The compound of claim 17, wherein the cyanine label is Cy5.

19. The compound of claim 1, wherein T is a peptidic targeting element.

20. The compound of claim 5, wherein $L_1$ is an optionally substituted alkyl linker, wherein each carbon atom is optionally replaced with a heteroatom.

21. The compound of claim 5, wherein $AA_1$ is an aralkyl amino acid side chain, optionally substituted with 1 to 3 A groups.

22. The compound of claim 5, wherein U is O.

* * * * *

UNITED STATES PATENT AND TRADEMARK OFFICE
CERTIFICATE OF CORRECTION

PATENT NO. : 10,100,037 B2
APPLICATION NO. : 14/777024
DATED : October 16, 2018
INVENTOR(S) : Matthew S. Bogyo and Martijn Verdoes It is certified that error appears in the above-identified patent and that said Letters Patent is hereby corrected as shown below:

In the Claims

Column 59, Line 31 In Claim 1, add "L is".

Signed and Sealed this
Twelfth Day of September, 2023

Katherine Kelly Vidal
*Director of the United States Patent and Trademark Office*